US011473152B2

(12) United States Patent
Chan et al.

(10) Patent No.: US 11,473,152 B2
(45) Date of Patent: Oct. 18, 2022

(54) METAL NANOSHELL-COATED BARCODES

(71) Applicant: The Governing Council of the University of Toronto, Toronto (CA)

(72) Inventors: Warren Che War Chan, Toronto (CA); Leo Y. T. Chou, Toronto (CA); Kun Chen, Toronto (CA)

(73) Assignee: The Governing Council of the University of Toronto

( * ) Notice: Subject to any disclaimer, the term of this patent is extended or adjusted under 35 U.S.C. 154(b) by 1270 days.

(21) Appl. No.: 14/768,051

(22) PCT Filed: Feb. 14, 2014

(86) PCT No.: PCT/CA2014/050108
§ 371 (c)(1),
(2) Date: Aug. 14, 2015

(87) PCT Pub. No.: WO2014/124543
PCT Pub. Date: Aug. 21, 2014

(65) Prior Publication Data
US 2019/0153545 A1 May 23, 2019

Related U.S. Application Data

(60) Provisional application No. 61/765,366, filed on Feb. 15, 2013.

(30) Foreign Application Priority Data

Dec. 11, 2013 (WO) ................. PCT/CA2013/050953

(51) Int. Cl.
*C12Q 1/6888* (2018.01)
*B82Y 30/00* (2011.01)
(Continued)

(52) U.S. Cl.
CPC ............ *C12Q 1/6888* (2013.01); *B82Y 30/00* (2013.01); *C09K 11/025* (2013.01);
(Continued)

(58) Field of Classification Search
CPC ..................... G01N 33/54313; C12Q 1/6888; B82Y 20/00; C09K 11/025; C09K 11/883; B01J 2219/005; C40B 20/04
See application file for complete search history.

(56) References Cited

U.S. PATENT DOCUMENTS

5,866,430 A * 2/1999 Grow ...................... G01N 21/65
436/172
2007/0037215 A1 * 2/2007 Patton ...................... C12Q 1/42
435/7.1
(Continued)

FOREIGN PATENT DOCUMENTS

| CA | 2693055 | 1/2009 |
| WO | 02079490 | 10/2002 |
| WO | 2008033804 | 3/2008 |

OTHER PUBLICATIONS

Sigma-Aldrich, 2002-2003, p. 1730 (Year: 2002).*
(Continued)

*Primary Examiner* — Narayan K Bhat
(74) *Attorney, Agent, or Firm* — Dorsey & Whitney LLP

(57) ABSTRACT

The present invention relates to barcodes coated with metal nanoshells and to methods of making the metal nanoshell-coated barcodes. The metal nanoshell-coated barcodes of the present invention have applications in detection systems, including multiplex detection systems.

10 Claims, 15 Drawing Sheets

Specification includes a Sequence Listing.

(51) Int. Cl.
| | |
|---|---|
| G01N 33/533 | (2006.01) |
| G01N 33/553 | (2006.01) |
| C09K 11/02 | (2006.01) |
| C09K 11/88 | (2006.01) |
| B82Y 15/00 | (2011.01) |
| B82Y 20/00 | (2011.01) |
| B82Y 40/00 | (2011.01) |

(52) U.S. Cl.
CPC .......... *C09K 11/883* (2013.01); *G01N 33/533* (2013.01); *G01N 33/553* (2013.01); *B82Y 15/00* (2013.01); *B82Y 20/00* (2013.01); *B82Y 40/00* (2013.01)

(56) References Cited

U.S. PATENT DOCUMENTS

| | | | | |
|---|---|---|---|---|
| 2009/0302235 | A1* | 12/2009 | Himmelhaus | G01N 21/6428 250/458.1 |
| 2012/0156490 | A1* | 6/2012 | Fournier-Bidoz | C40B 20/04 428/402 |

OTHER PUBLICATIONS

Nair et al. "Improving biocatalytic activity of enzyme-loaded nanofibers by dispersing entangled nanofiber structure" Biomacromolecules, 2007, 8: 1266-1270 (Year: 2007).*

Chen et al (Post art), Fabrication of metal nanoshell quantum-dot barcodes for biomolecular detection, 2013, Nano Today, 8, 228-234. (Year: 2013).*

Wilson, R., et al. (2006) Encoded microcarriers for high-throughput multiplexed detection. Angewandte Chemie International Edition, 45:6104-6117.

Han, M., et al. (2001) Quantum-dot-tagged microbeads for multiplexed optical coding of biomolecules. Nature Biotechnology,19:631-635.

Fournier-Bidoz, S., et al. (2008) Facile and rapid one-step mass preparation of quantum-dot barcodes. Angewandte Chemie International Edition, 47:5577-5581.

Gao, S. and Nie, S. (2003) Doping Mesoporous Materials with Multicolor Quantum Dots. The Journal of Physical Chemistry B, 107:11575-11578.

Wang, D., et al. (2002) Semiconductor Quantum Dot Labeled Microsphere Bioconjugates Prepared by Stepwise Self-Assembly. Nano Letters, 2:857-861.

Gao, X., et al. (2002) Quantum-dot nanocrystals for ultrasensitive biological labeling and multicolor optical encoding. Journal of Biomedical Optics, 7:532-537.

Lee, J.A., et al. (2007) Toward the Accurate Read-out of Quantum Dot Barcodes: Design of Deconvolution Algorithms and Assessment of Fluorescence Signals in Buffer. Advanced Materials, 19:3113-3118.

Chou, L.Y. and Chan, W.C. (2011) A strategy to assemble nanoparticles with polymers for mitigating cytotoxicity and enabling size tuning. Nanomedicine (Land), 6:767-775.

Brust, M., et al. (1995) Novel gold-dithiol nano-networks with non-metallic electronic properties. Advanced Materials, 7:795-797.

Cao, Y. C., et al. (2006) Preparation of Au coated polystyrene beads and their application in an immunoassay. Journal of Immunological Methods, 317:163-170.

Ji, T., et al. (2001) Preparation, Characterization, and Application of Au-Shell/Polystyrene Beads and Au-Shell/Magnetic Beads. Advanced Materials, 13:1253-1256.

Lee, J.H., et al. (2009) Facile Preparation of Highly-Scattering Metal Nanoparticle-Coated Polymer Microbeads and Their Surface Plasmon Resonance. Journal of the American Chemical Society, 131:5048-5049.

Peceros, K.E.S., et al. (2005) Dipole-dipole plasmon interactions in gold-on-polystyrene composites. The Journal of Physical Chemistry B,109:21516-21520.

Quach, A.D., et al. (2011) Gold Nanoparticle-Quantum Dot-Polystyrene Microspheres as Fluorescence Resonance Energy Transfer Probes for Bioassays. Journal of the American Chemical Society, 133:2028-2030.

Shi, W., et al. (2005) Gold nanoshells on polystyrene cores for control of surface plasmon resonance. Langmuir, 21:1610-1617.

Gao, Y., et al. (2011) Quantum-dot-encoded microbeads for multiplexed genetic detection of non-amplified DNA samples. Small, 7:137-146.

Giri, S., et al. (2011) Rapid screening of genetic biomarkers of infectious agents using quantum dot barcodes. ACS Nano, 5:1580-1587.

Dragan, A.I., et al. (2010) Metal-enhanced PicoGreen fluorescence: application for double-stranded DNA quantification. Analytical Biochemistry, 396:8-12.

Sabanayagam, C.R., et al. (2007) Increasing the sensitivity of DNA microarrays by metal-enhanced fluorescence using surface-bound silver nanoparticles. Nucleic Acids Research, 35:e13, p. 1-9.

Matveeva, E.G., et al. (2007) Metal particle-enhanced fluorescent immunoassays on metal mirrors. Analytical Biochemistry, 363:239-245.

Zhang, J., et al. (2005) Metal-enhanced fluoroimmunoassay on a silver film by vapor deposition. The Journal of Physical Chemistry B, 109:7969-7995.

Kockaerts, Y., et al. (2001) Imported malaria in the 1990s: a review of 101 patients. European Journal of Emergency Medicine, 8:287-290.

Martens, P., et al. (2000) Malaria on the move: human population movement and malaria transmission. Emerging Infectious Diseases, 6:103-109.

Ndao, M., et al. (2004) Comparison of Blood Smear, Antigen Detection, and Nested-PCR Methods for Screening Refugees from Regions Where Malaria is Endemic after a Malaria Outbreak in Quebec, Canada. Journal of Clinical Microbiology, 42:2694-2700.

Snounou, G., et al. (1993) High sensitivity of detection of human malaria parasites by the use of nested polymerase chain reaction. Molecular and Biochemical Parasitology, 61:315-320.

Hill, H.D., et al. (2009) The Role Radius of Curvature Plays in Thiolated Oligonucleotide Loading on Gold Nanoparticles. ACS Nano, 3:418-424.

Wilson, M.L. (2012) Malaria rapid diagnostic tests. Clinical Infectious Diseases, 54:1637-1641.

McMorrow, M.L., et al. (2011) Malaria rapid diagnostic tests in elimination settings—can they find the last parasite? Clinical Microbiology and Infection, 17:1624-1631.

Chapin, S.C., et al. (2011) Ultrasensitive Multiplexed MicroRNA Quantification on Encoded Gel Microparticles Using Rolling Circle Amplification. Analytical Chemistry, 83:7179-7185.

Schopf, E., et al. (2010) Attomole DNA detection assay via rolling circle amplification and single molecule detection. Analytical Biochemistry, 397:115-117.

Peng, X., et al. (1997) Epitaxial Growth of Highly Luminescent CdSe/CdS Core/Shell Nanocrystals with Photostability and Electronic Accessibility. Journal of the American Chemical Society, 119:7019-7029.

* cited by examiner

☐ poly(styrene-co-maleic anhydride) single polymer
▨ poly(styrene-co-maleic anhydride) - polystyrene mixed polymers

METAL NANOSHELL-COATED BARCODES

CROSS REFERENCE TO RELATED APPLICATIONS

This application is a national stage application under 35 U.S.C. 371 of International Application No. PCT/CA2014/050108 filed Feb. 14, 2014, which in turn claims the benefit under 35 U.S.C. 119(e) of U.S. Provisional Ser. No. U.S. 61/765,366, filed Feb. 15, 2013 and PCT/CA2013/050953, the contents of each of which are hereby incorporated by reference into the present disclosure.

FIELD OF THE INVENTION

The present disclosure relates to the field of barcodes and to methods of producing barcodes. More particularly, the present disclosure relates to metal nanoshell-coated barcodes.

BACKGROUND OF THE INVENTION

Polymer microbeads are one of the most versatile platforms for chemical and biosensing applications. Microbead platforms provide faster reaction kinetics, higher throughput capacity for biomolecule conjugation, and better assay reproducibility compared to other detection techniques [1]. When microbeads are doped with organic fluorophores or quantum dots (QDs) to create barcodes, they could detect thousands of molecules simultaneously. Organic fluorophore-barcoded microbeads are becoming the cornerstone of multiplex detection schemes. A limitation of these barcodes include the requirement for complex and expensive read-out instruments to compensate for the requirement of light sources for exciting the different fluorophores and these barcodes can only be used in specific environmental conditions because the emission properties of the different fluorophores are influenced by the assay environment. This limitation can be overcome by using QDs to create the barcodes. Over 40,000 different barcodes could be engineered with QDs of six different colors and intensity levels and they could be excited with a single wavelength [2]. Such an extensive multiplex detection technology would be extremely useful in rapid analysis of a variety of mechanisms and high-throughput screening of organic and inorganic markers. There are currently many proposed methods for engineering QD barcodes [2-5], but none of these methods have produced QD barcodes that can be easily conjugated, and have a good shelf life and fluorescence consistency in different temperatures, buffers or assay environments to enable this technology to be broadly used. Any change in the QD fluorescence during the assay process could lead to the misidentification of the barcodes [6,7]. Therefore, QD barcoding technology remains in the research phase and has not advanced for broader utility.

The applicants previously showed that the fluorescence of QDs does not change in different assay conditions when they are at the center of sub-100 nm polystyrene beads [8]. Unfortunately, this synthetic method cannot be adapted to prepare larger beads. When attempting to use a similar strategy for preparing larger QD barcodes, the initiators quenched or altered the QDs fluorescence properties during the reaction. However, this study demonstrated that QDs sheltered deep inside a polystyrene bead would protect the QDs from interacting with the aqueous environment.

As such, an object of the invention is to overcome the above limitations by providing barcodes having stability or improved stability relative to the barcodes of the prior art, against degradation and analytical sensitivity, and to simplify the conjugation process.

Further and other objects of the invention will be realized from the following Summary of the Invention, the Description of the Invention and the embodiments and Examples thereof.

SUMMARY OF THE INVENTION

In one embodiment, the present invention provides for a barcode, which may be used in methods for detecting one or more targets of interest in a sample and in multiplex systems for detecting one or more targets of interest. The barcode of the present invention, in one embodiment, includes a metal nanoshell-coated microbead having one or more populations of fluorophores.

In one embodiment of the barcodes of the present invention, the fluorophores include organic fluorophores, inorganic fluorophores, or a mixture of organic and inorganic fluorophores.

In another embodiment of the barcodes of the present invention, the microbead is a polymeric microbead.

In another embodiment of the barcodes of the present invention, the microbead comprises a single polymer system of poly(styrene-co-maleic anhydride).

In another embodiment of the barcodes of the present invention, the microbead comprises a mixed polymer system of polystyrene and poly(styrene-co-maleic anhydride).

In another embodiment of the barcodes of the present invention, the ratio between polystyrene and poly(styrene-co-maleic anhydride) ranges between about 4:1 to about 1:1 in mass.

In another embodiment of the barcodes of the present invention, the polymers include analogues or derivatives.

In another embodiment of the barcodes of the present invention, the fluorophores are quantum dots (QDs).

In another embodiment of the barcodes of the present invention, the metal is selected from silver or gold.

In another embodiment of the barcodes of the present invention, the barcode further comprises a target-specific capture probe conjugated to the metal nanoshell.

In another embodiment of the barcodes of the present invention, the target includes inorganic and organic materials.

In another embodiment of the barcodes of the present invention, the organic materials include unicellular and multicellular organisms and any components thereof, peptides, proteins, oligosaccharides, lipids, genes, nucleic acids, amino acids, and wherein the inorganic materials include inorganic molecules having metal atoms.

In another embodiment of the barcodes of the present invention, the barcode includes a protein layer between a surface of the microbead and the metal nanoshell.

In another embodiment of the barcodes of the present invention, the metal nanoshell operates to enhance shelf-life of the barcode relative to the barcode without the metal nanoshell.

In another embodiment of the barcodes of the present invention, the metal nanoshell operates to enhance fluorescence stability of the barcode relative to the barcode without the metal nanoshell.

In another embodiment of the barcodes of the present invention, the metal nanoshell has a thickness of about 20 nm to about 80 nm.

In one embodiment the present invention provides for a method of growing a metal nanoshell on the surface of a barcode. In one embodiment, the method of growing a metal nanoshell on the surface of a barcode includes: (a) contacting the barcode with metal nanoparticles, and (b) mixing the barcode obtained in step (a) with a salt of the metal for a time sufficient for growing the metal nanoshell on the barcode.

In one embodiment of the method of growing a metal nanoshell on the surface of a barcode, the barcode includes a microbead having one or more populations of fluorophores, and the fluorophores include organic fluorophores, inorganic fluorophores, or a mixture of organic and inorganic fluorophores.

In another embodiment of the method of growing a metal nanoshell on the surface of a barcode, the microbead is a polymeric microbead.

In another embodiment of the method of growing a metal nanoshell on the surface of a barcode, the microbead comprises a single polymer system of poly(styrene-co-maleic anhydride).

In another embodiment of the method of growing a metal nanoshell on the surface of a barcode, the microbead comprises a mixed polymer system of polystyrene and poly(styrene-co-maleic anhydride).

In another embodiment of the method of growing a metal nanoshell on the surface of a barcode, the ratio between polystyrene and poly(styrene-co-maleic anhydride) ranges between about 4:1 to about 1:1 in mass.

In another embodiment of the method of growing a metal nanoshell on the surface of a barcode of the present invention, the polymers include analogues or derivatives.

In another embodiment of the method of growing a metal nanoshell on the surface of a barcode, the fluorophores are QDs.

In another embodiment of the method of growing a metal nanoshell on the surface of a barcode, the metal is selected from silver or gold.

In another embodiment of the method of growing a metal nanoshell on the surface of a barcode, the method further includes functionalizing the metal nanoshell-coated barcode by conjugating a capture probe to the metal nanoshell, wherein said capture probe is capable of interacting with a target.

In another embodiment of the method of growing a metal nanoshell on the surface of a barcode, the target includes inorganic materials and organic materials.

In another embodiment of the method of growing a metal nanoshell on the surface of a barcode, the organic materials include unicellular and multicellular organisms and any components thereof, peptides, proteins, oligosaccharides, lipids, genes, nucleic acids, amino acids, and wherein the inorganic materials include inorganic molecules having metal atoms.

In another embodiment of the method of growing a metal nanoshell on the surface of a barcode, the method further includes adding a protein layer on the barcode prior to contacting the barcode with the metal nanoparticles.

In another embodiment of the method of growing a metal nanoshell on the surface of a barcode, the time of step (b) is the time required for growing the metal nanoshell corresponding to a pre-selected thickness of the metal nanoshell.

In another embodiment of the method of growing a metal nanoshell on the surface of a barcode, the time required for growing the metal nanoshell is selected from a standard curve that compares metal nanoshell thickness and growth time of the metal nanoshell.

In one embodiment, the present invention provides for a detection system for detecting a target in a sample. The detection system, in one embodiment, includes a plurality of barcodes, each barcode comprising a metal nanoshell-coated microbead having one or more populations of fluorophores and a capture probe conjugated to the metal nanoshell, the capture probe being capable of interacting with the target and the system being capable of producing a detectable signal that indicates detection of the target in the sample, the detectable signal being comprised of a first signal from the barcode having the capture probe bound to the target and a second signal from a secondary probe bound to the target.

In one embodiment of the detection system of the present invention, the detection system further includes a wireless communication device, the wireless communication device including means for collecting the detectable signals from the plurality of barcodes and secondary probes.

In another embodiment of the detection system of the present invention, the wireless communication device further includes one or both means for analyzing the collected signals from the plurality of barcodes and secondary probes, and means to transmit the collected signals for remote analysis.

In another embodiment of the detection system of the present invention, the detection system further includes the secondary probe signal, the secondary probe signal indicating successful capture of the target by the barcode capture probe.

In one embodiment, the present invention provides for a multiplex detection system for simultaneously detecting multiple targets of interest in a single sample. The multiplex detection system of the present invention, in one embodiment, includes: a plurality of barcodes, each barcode comprising: (i) a metal nanoshell-coated microbead having one or more populations of fluorophores and (ii) one capture probe conjugated to the surface of the barcode capable of interacting with one of the multiple targets of interest such that the plurality of barcodes include at least one barcode for each of the multiple targets of interest, the plurality of metal nanoshell-barcodes being capable of producing different target-specific signals for each of the multiple targets of interest, each target-specific signal being comprised of a first signal from the barcode having the capture probe interacting with a particular target of interest, and a second signal from a secondary probe bound to the particular target of interest.

In one embodiment of the multiplex detection system of the present invention, the multiplex detection system further includes the secondary probe signal, the secondary probe signal indicating successful capture of the target by the barcode capture probe.

In another embodiment of the multiplex detection system of the present invention, the multiplex detection system further includes a wireless communication device, the wireless communication device including means for collecting the first signals from the plurality of barcodes and the second signals from the secondary probe signal.

In another embodiment of the multiplex detection system of the present invention, the wireless communication device further includes one or both means for analyzing the collected signals from the plurality of barcodes and secondary probes, and means to transmit the collected signals for remote analysis.

The present invention, in another embodiment, provides for a method of detecting a target of interest in a sample. The method, in one embodiment, includes: contacting the sample with: (a) a plurality of barcodes, each barcode comprising a metal nanoshell-coated microbead having one or more populations of fluorophores, and a capture probe conjugated to the metal nanoshell, the capture probe being capable of interacting with the target of interest, each barcode being capable of emitting a target-specific signal, and (b) a secondary probe, the secondary probe being capable interacting with the target of interest and of emitting a secondary probe signal; wherein the presence of the barcode signal and the secondary probe signal indicates detection of the target in the sample.

In one embodiment of the method of detecting a target of interest in a sample, the barcode comprises a microbead having one or more populations of fluorophores and wherein the fluorophores include organic fluorophores, inorganic fluorophores, or a mixture of organic and inorganic fluorophores.

In another embodiment of the method of detecting a target of interest in a sample, the microbead is a polymeric microbead.

In another embodiment of the method of detecting a target of interest in a sample, the microbead comprises a single polymer system of poly(styrene-co-maleic anhydride).

In another embodiment of the method for detecting a target of interest in a sample, the microbead comprises a mixed polymer system of polystyrene and poly(styrene-co-maleic anhydride).

In another embodiment of the method of detecting a target of interest in a sample, the ratio between polystyrene and poly(styrene-co-maleic anhydride) ranges between about 4:1 to about 1:1 in mass.

In another embodiment of the method of detecting a target of interest in a sample, the polymers include analogues or derivatives.

In another embodiment of the method of detecting a target of interest in a sample, the fluorophores are QDs.

In another embodiment of the method of detecting a target of interest in a sample, the metal is selected from silver or gold.

In another embodiment of the method of detecting a target of interest in a sample, the target includes inorganic materials and organic materials.

In another embodiment of the method of detecting a target of interest in a sample, the organic materials include unicellular and multicellular organisms and any components thereof, peptides, proteins, oligosaccharides, lipids, genes, nucleic acids, amino acids, and wherein the inorganic materials include inorganic molecules having metal atoms.

In another embodiment of the method of detecting a target of interest in a sample, the barcode includes a protein layer between a surface of the microbead and the metal nanoshell.

In another embodiment of the method of detecting a target of interest in a sample, the metal nanoshell has a thickness of about 20 nm to about 80 nm.

In one aspect of the present invention, the samples are biological or non-biological samples.

In another aspect of the present invention, the samples are non-human samples.

In another aspect of the present invention, the samples are human samples.

In another aspect of the present invention, the samples are solid or fluid samples.

In another aspect of the present invention, the samples are biological or non-biological, wherein the biological samples include solid, liquid or gaseous samples taken from a unicellular or multi-cellular organism of the animal or plant kingdoms, including prokaryote and eucaryote organisms, and wherein the non-biological samples include water samples, soil samples, gaseous samples and mineral samples.

BRIEF DESCRIPTION OF THE DRAWINGS

Embodiments will now be described, by way of example only, with reference to the drawings, in which.

right column (graphs c, f, i): silver nanoshell-coated poly(styrene-co-maleic anhydride)-polystyrene mixed polymers.

Figure 3:
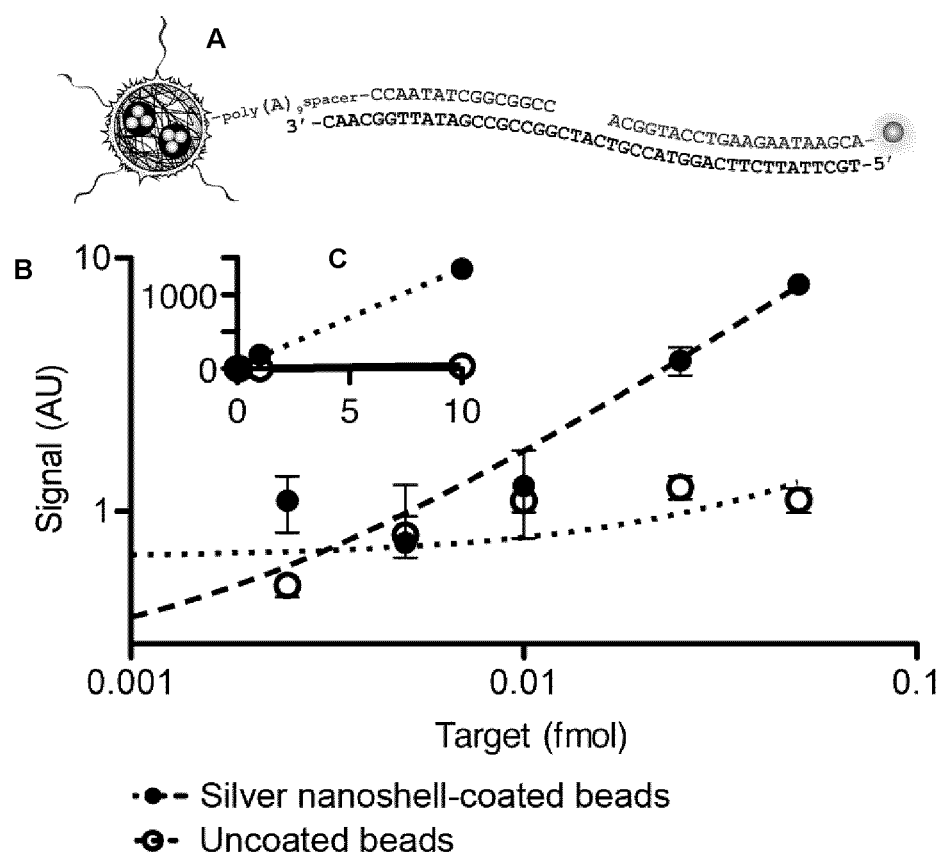

FIG. 3: (A) is Graph illustrating a scheme of a sandwich assay. (B) Graph illustrating the comparison of assay sensitivities using uncoated and silver nanoshell-coated microbeads. (C (inset figure)) Up to 10 femtomoles of target were measured. Black solid dots and hollow circles represent the silver nanoshell-coated beads and uncoated beads, respectively.

Figure 4:
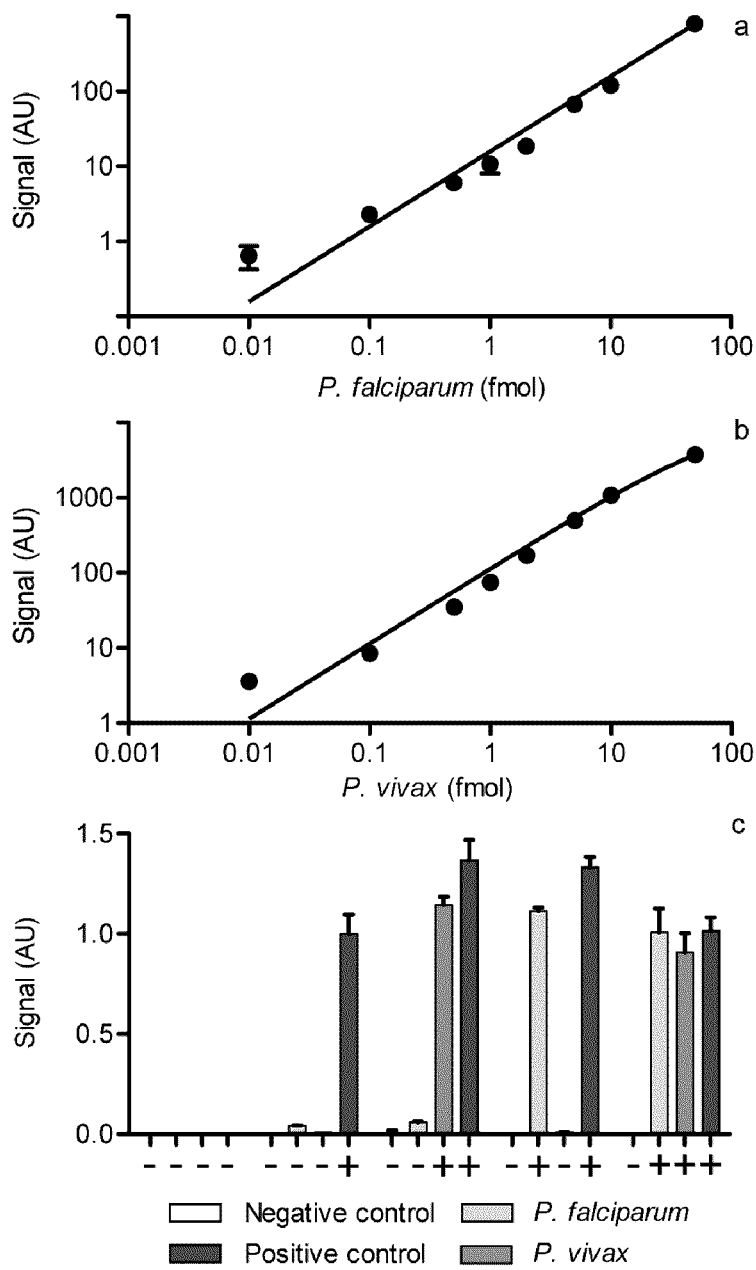

FIG. 4 are graphs illustrating multiplexed detection of DNA targets by silver nanoshell-coated QD barcodes. Graphs (a) and (b) are the dose-response curves of *P. falciparum* and *P. vivax*, DNA sequences respectively. Graph (c) Multiplexed illustrates multiplexed detection of DNA targets.

Figure 5:
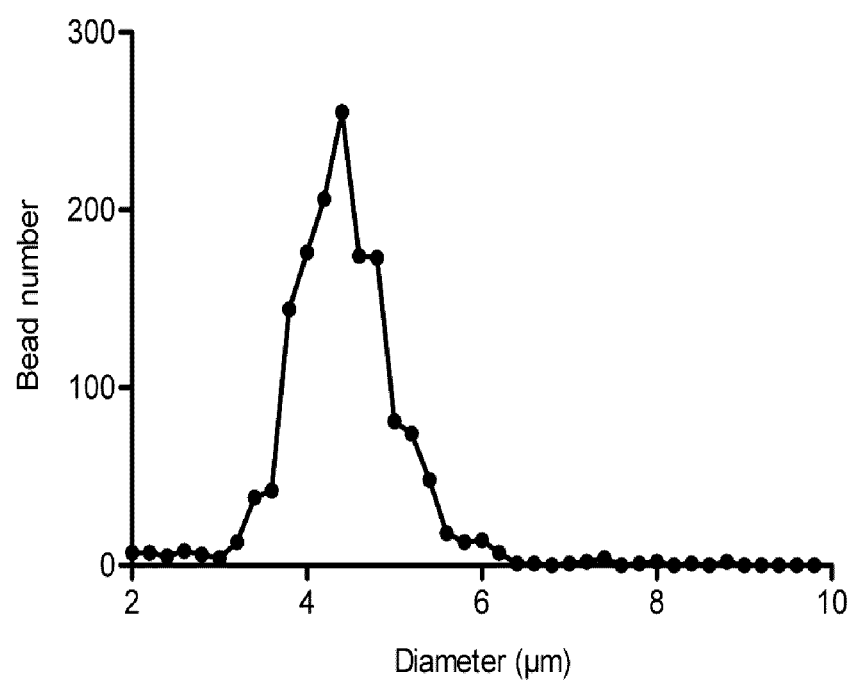

FIG. 5 is a size histogram of the barcodes illustrating size distribution of QD barcodes. The diameter and concentration of uncoated QD barcodes were determined by a Vi-cell analyzer. The diameter in the above graph was 4.5±0.7 nm (median±standard deviation).

Figure 6:
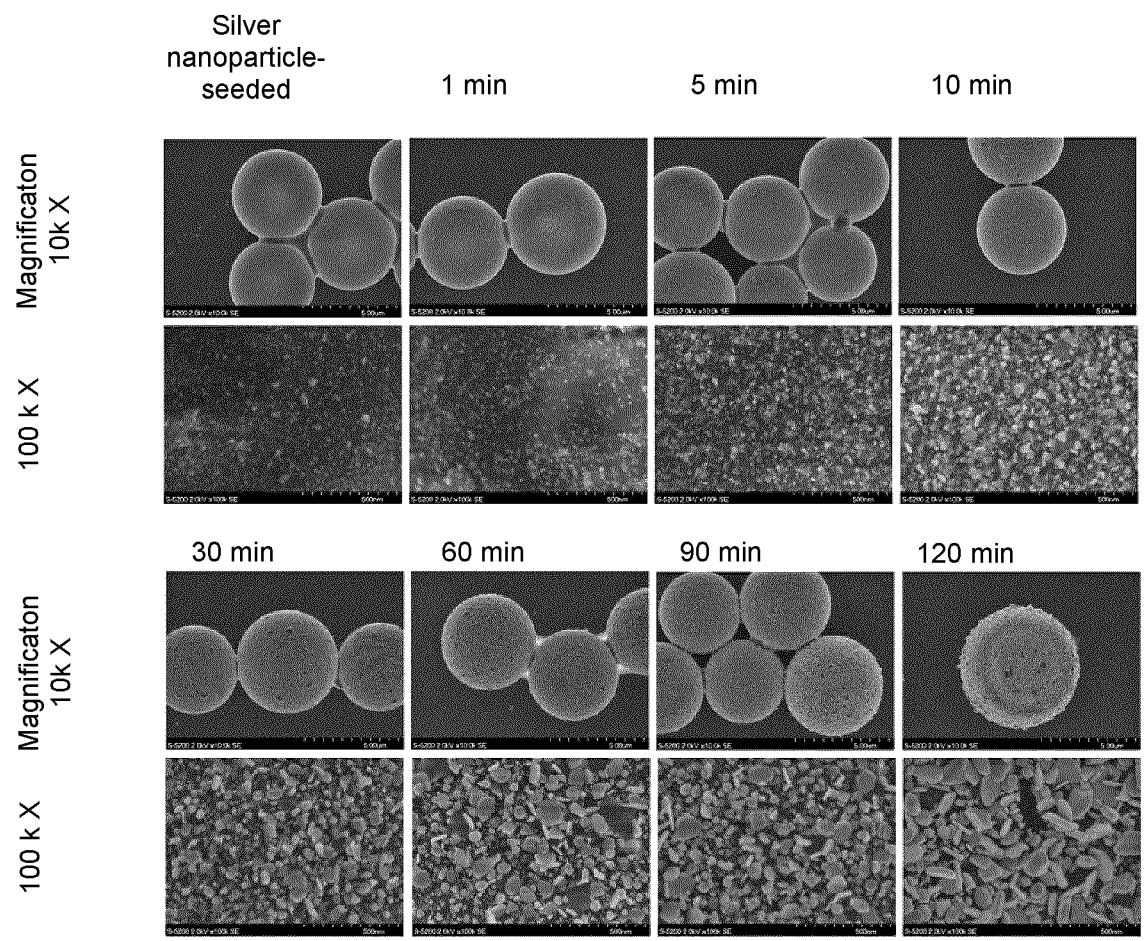

FIG. 6 are SEM images of silver nanoshell growth on beads over time. For each time point of growing, an image of a lower magnitude (10k ×) of magnification is shown in the top row and the corresponding zoomed-in image (100k ×) is shown below. The surface coverage of the silver nanoshell was correlated with the growing period.

Figure 7:
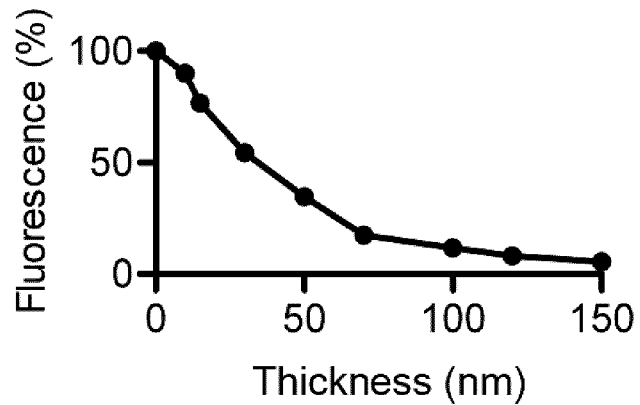

FIG. 7 is a graph illustrating the effect of silver nanoshell thickness on the fluorescence intensity of mixed-polymer QD barcodes.

Figure 8:
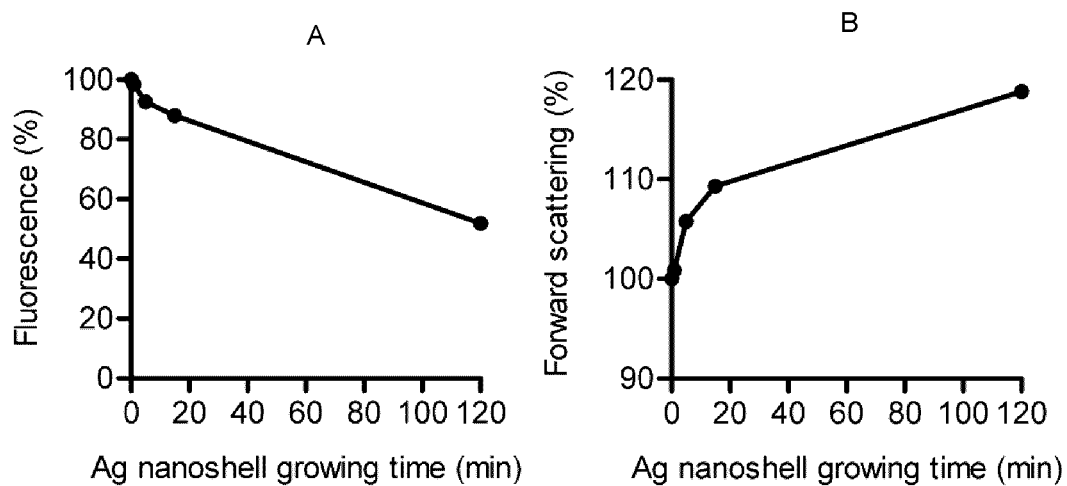

FIG. 8 are graphs illustrating the effect of silver nanoshell growing time on (A) the fluorescence intensity of QD600 barcodes, and (B) forward scattering.

Figure 9:
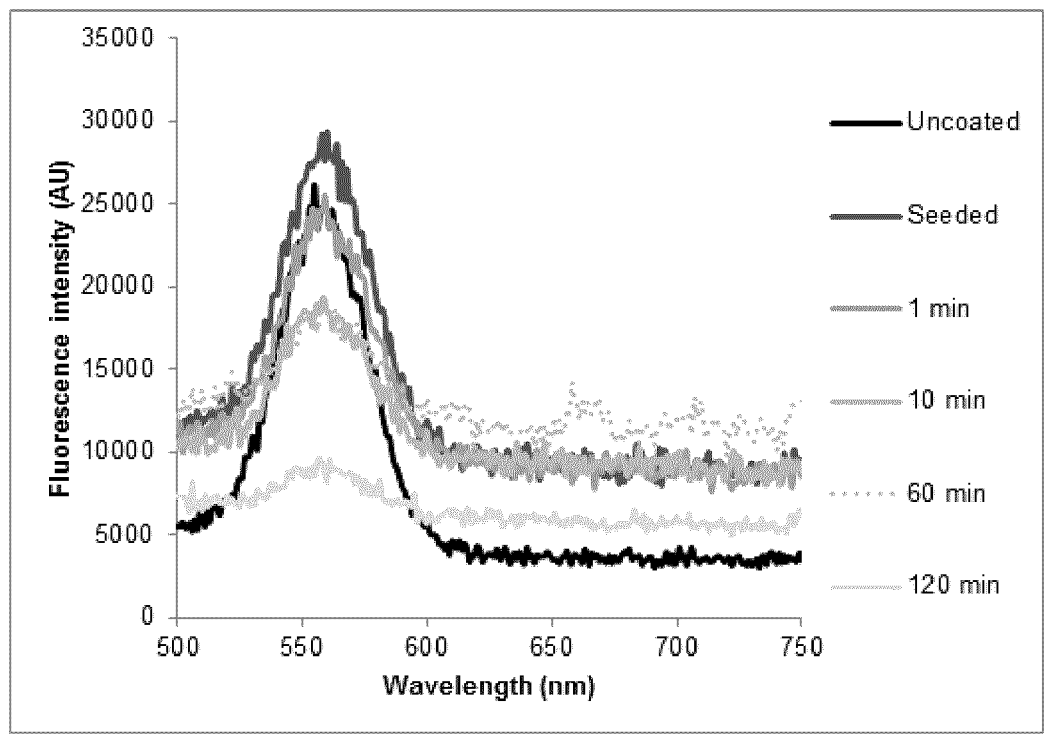

FIG. 9 illustrates (A) fluorescence and (B) absorbance spectra of QD barcodes during silver nanoshell growing.

Figure 10:
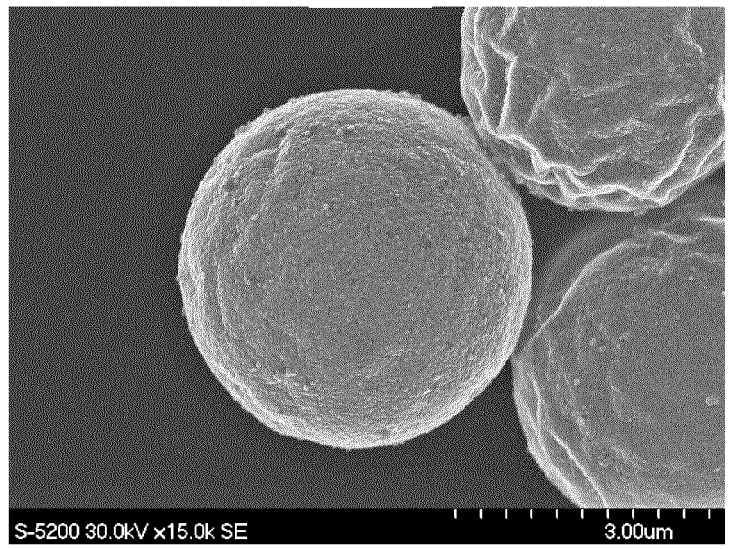
Figure 10:
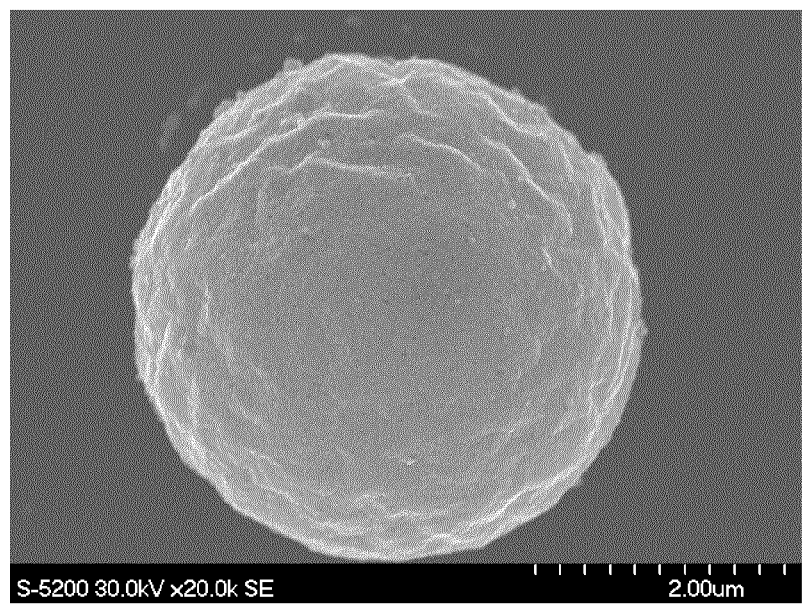

FIG. 10 are SEM images of gold nanoshell-coated microbeads in accordance to one embodiment of the present invention.

Figure 11:
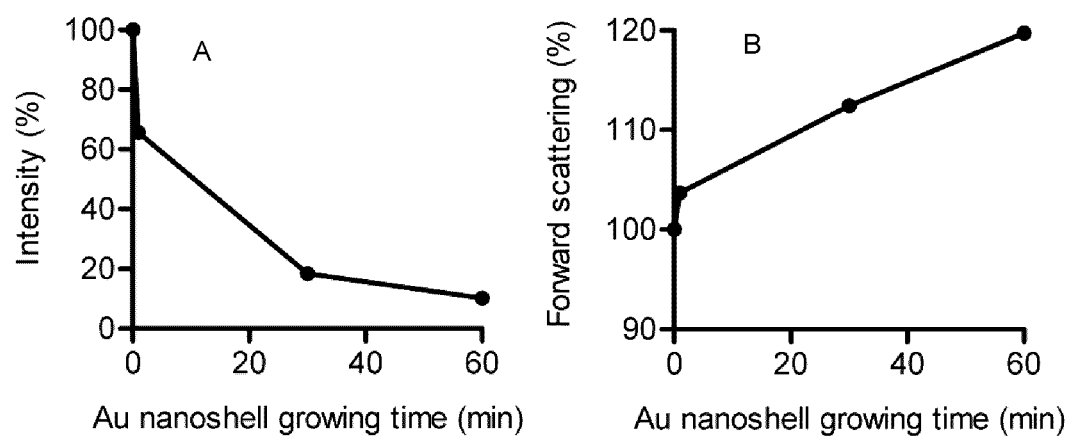

FIG. 11 are graphs illustrating the effect of gold nanoshell growing time on (A) fluorescence intensity of QD barcodes and (B) forward scattering of QD barcodes.

Figure 12:
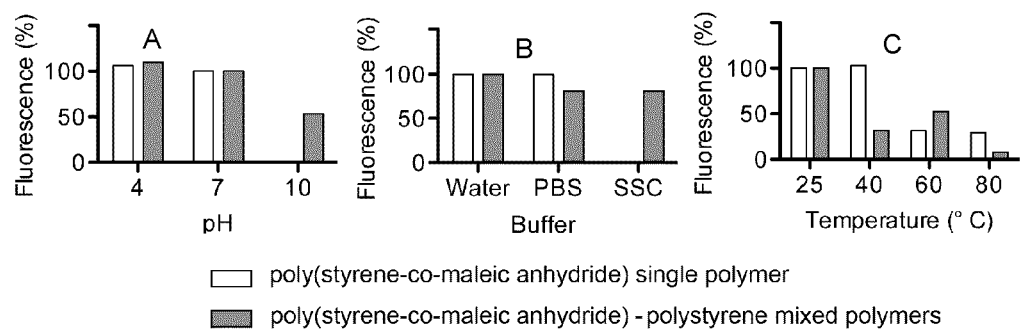

FIG. 12 are graphs illustrating fluorescence stabilities of uncoated QD barcodes made of single polymer and mixed polymers under different environmental conditions: (A)—pH, (B)—buffer, and (C)—temperature.

Figure 13:
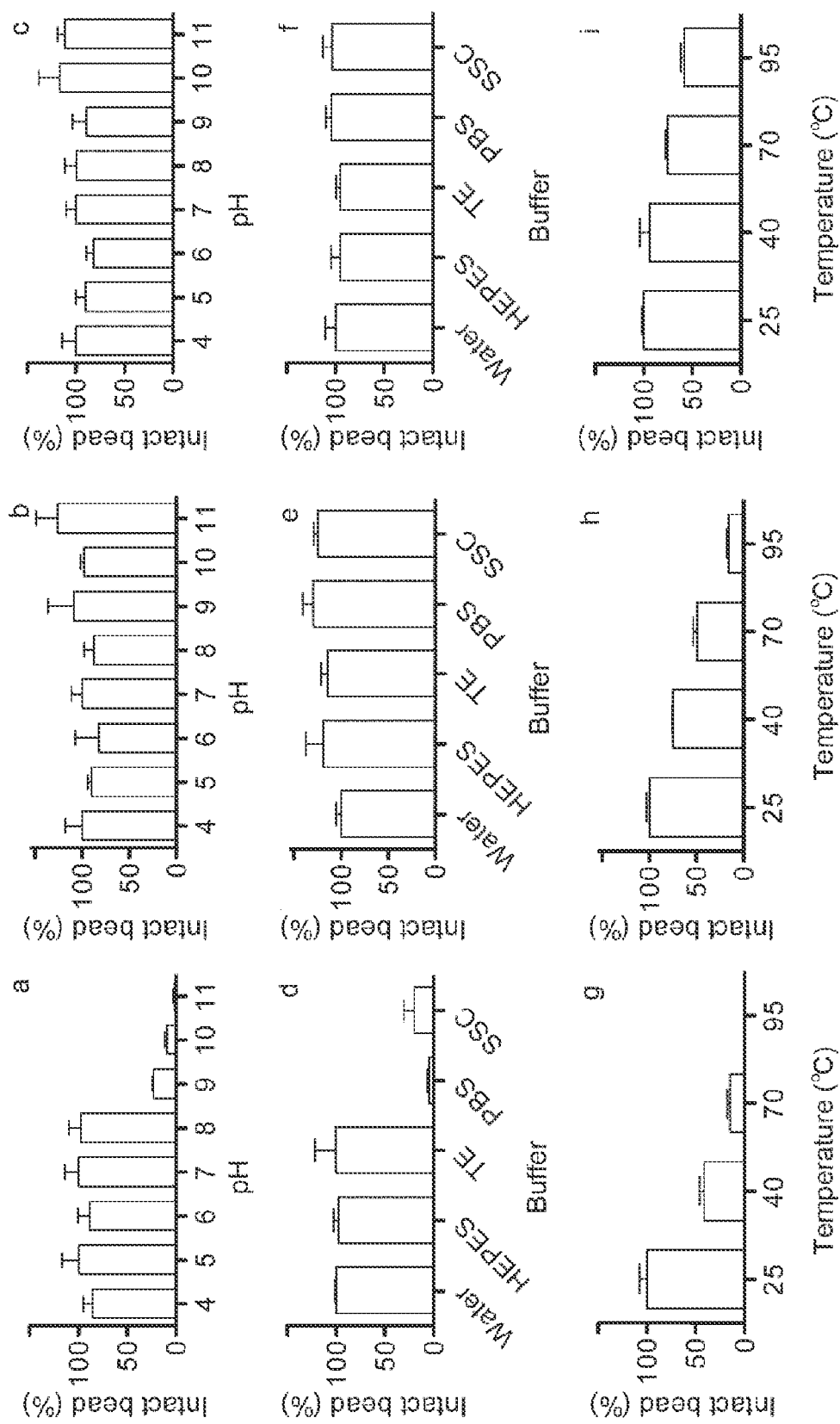

FIG. 13 The integrity of QD barcodes made from different compositions under different conditions. Left column (a, d, g): uncoated poly(styrene-co-maleic anhydride) single polymer; middle column (b, e, h): silver nanoshell-coated single polymer; right column (c, f, i): silver nanoshell-coated poly(styrene-co-maleic anhydride)-polystyrene mixed polymers. The silver nanoshells were 20-30 nm in thickness.

Figure 14:
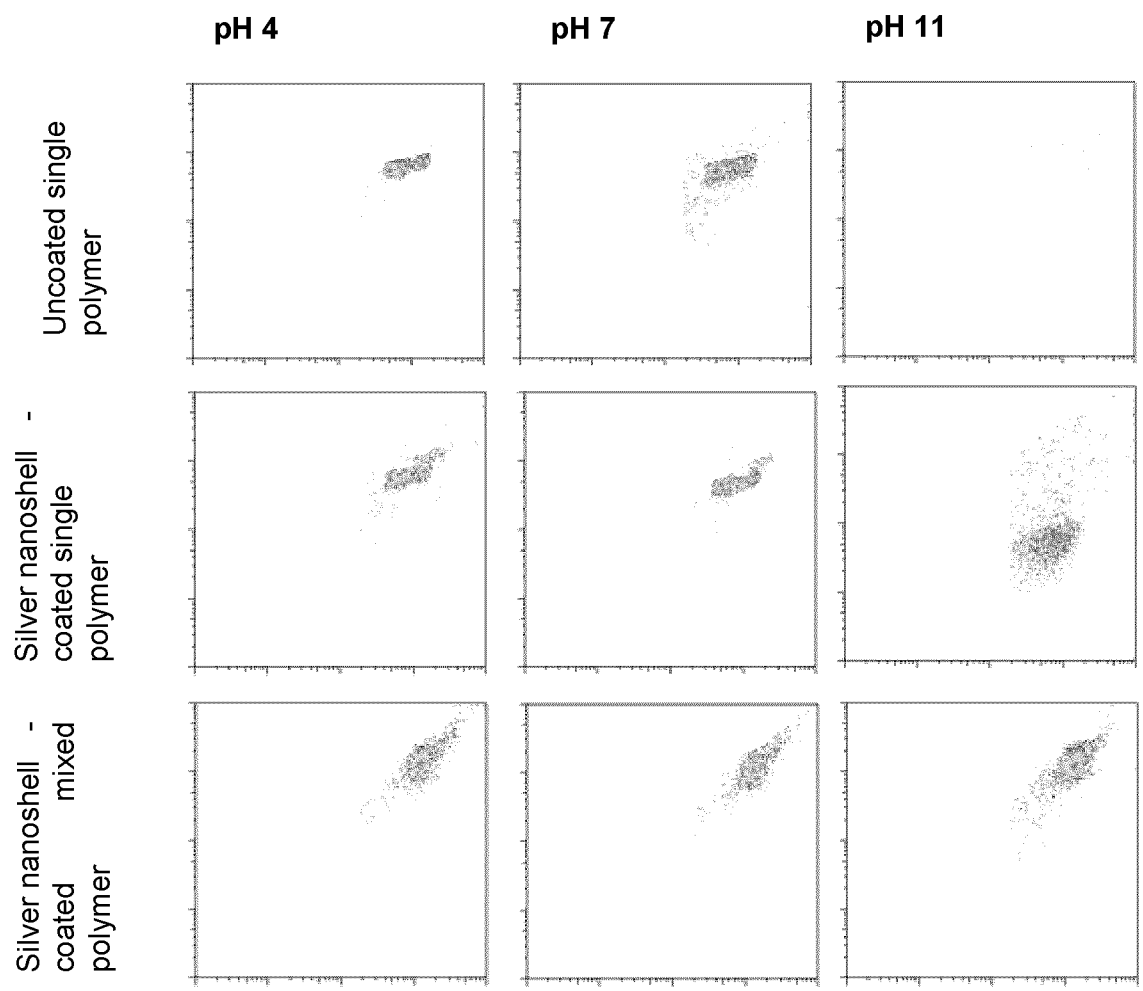

FIG. 14 are forwarding scattering (FSC)-side scattering (SSC) plots in flow cytometry.

Figure 15:
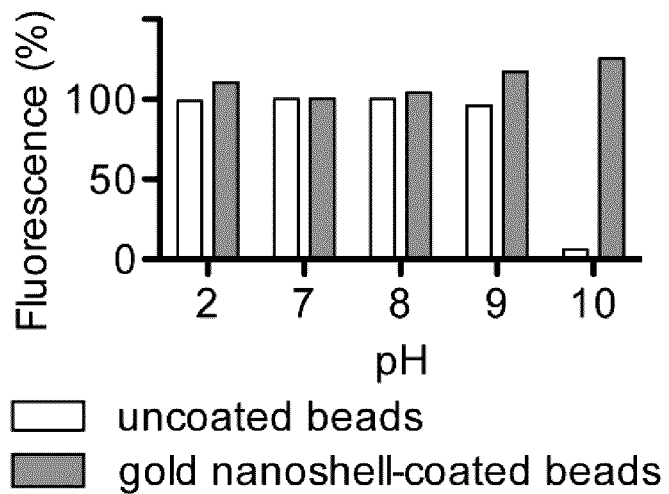

FIG. 15 is a graph illustrating the effect of gold nanoshells on the stability of barcode fluorescence under different pHs.

Figure 16:
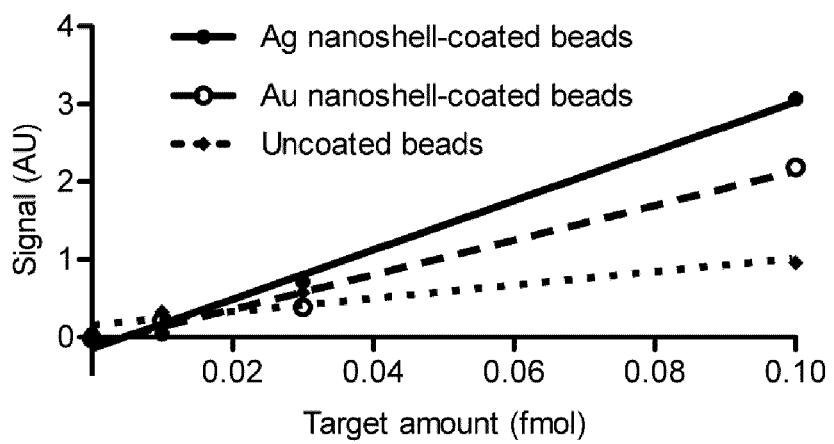

FIG. 16 is a graph illustrating a comparison of assay sensitivities using uncoated and silver or gold nanoshell-coated microbeads. The shell thickness was about 50 nm for both metals. The assays were carried out in parallel. Both metal nanoshells enhanced the assay performance as shown by the dose-response curves. The silver nanoshell-coated beads demonstrated the best assay performance among the three conditions.

Figure 17:
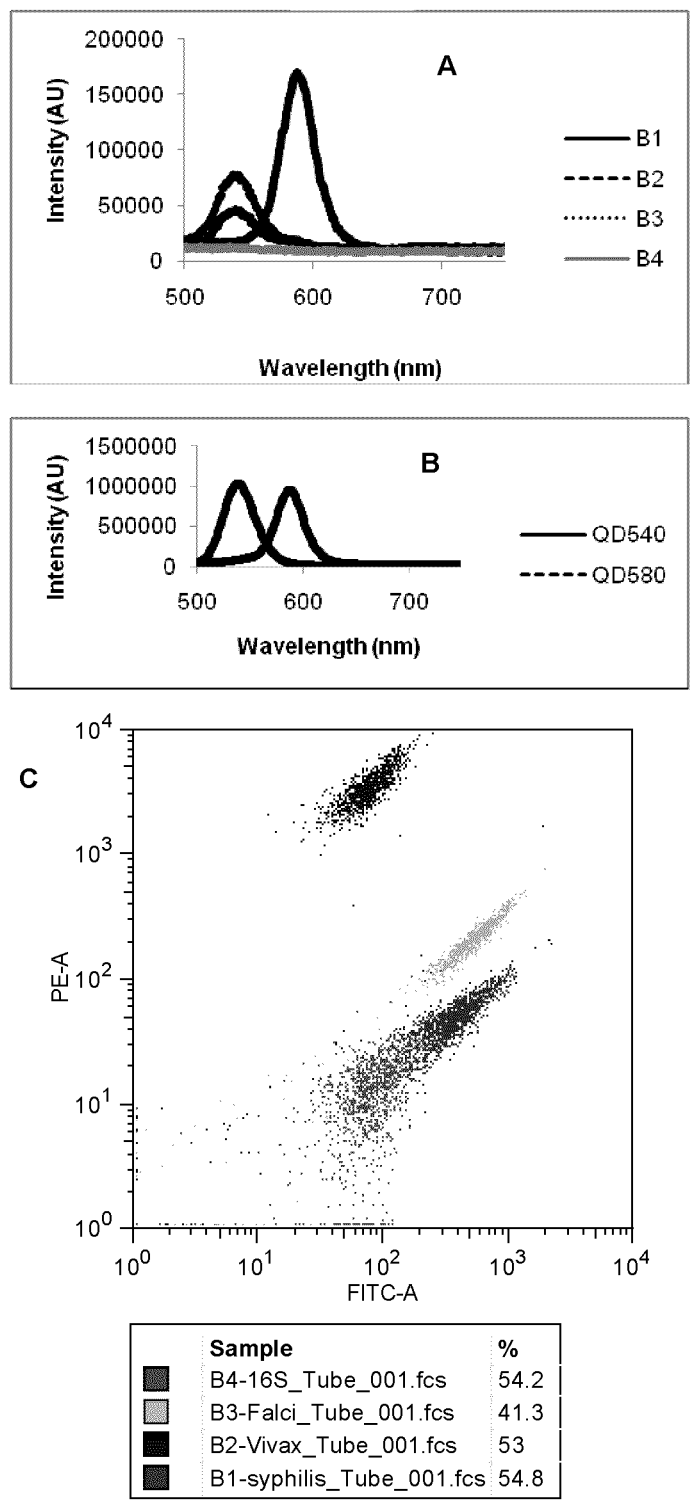

FIG. 17 are graphs illustrating the emission spectra of QDs and the 4-plex silver nanoshell-coated barcodes and their fluorescence plots in flow cytometry. The emission spectra of the QDs (QD530 and QD580) used for making the barcodes were measured by a fluorometer. By varying the intensities of these QDs, the inventors made four barcodes and their emission spectra were also determined. These barcodes showed distinct fluorescence intensity distributions in flow cytometer plots. The horizontal scale is the FITC channel (525 nm) intensity. The vertical scale is the PE channel (575 nm) intensity. Barcode 1 (B1) and 4 (B4) were the negative and positive control, respectively. B2 and B3 represent *P. vivax* and *P. falciparum*, respectively.

DETAILED DESCRIPTION OF THE INVENTION

Definitions

In this specification and in the claims that follow, reference will be made to a number of terms that shall be defined to have the meanings below. All numerical designations, e.g., dimensions and weight, including ranges, are approximations that typically may be varied (+) or (−) by increments of 0.1, 1.0, or 10.0, as appropriate. All numerical designations may be understood as preceded by the term "about". The singular form "a", "an", and "the" includes plural references unless the context clearly dictates otherwise. All publications cited herein, as well as the priority document, are incorporated by reference in their entirety.

"Capture probe" refers to a compound that binds a target molecule in a sample such that their relative expression levels can be detected. Capture probes may include nucleic acid sequences, proteins, phages, antibodies, enzymes and so forth. Targets may include organic molecules including nucleic acids, proteins, lipids, sugars, toxins, unicellular and multi-cellular organisms, viruses and components thereof and inorganic molecules, which may include metal atoms, and any other target of interest that can may be bound to a capture probe.

The term "secondary probe" refers to a molecule, which is capable of recognizing the target of a capture probe and of producing a detectable signal in response to the interaction between the capture probe, the target of said capture probe and the secondary probe. Secondary probes may include nucleic acid sequences, proteins, phages, antibodies, enzymes and so forth. The secondary probe may include a fluorescent molecule.

The term "comprising" means any recited elements are necessarily included and other elements may optionally be included. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

As used herein, a "quantum dot" (QD) is a semiconducting photoluminescent material, as is known in the art (for example, see Alivasatos, Science 271:933-937 (1996)). Non-limiting examples of QDs include: CdS quantum dots, CdSe quantum dots, CdSe/CdS core/shell quantum dots, CdSe/ZnS core/shell quantum dots, CdTe quantum dots, PbS quantum dots, and/or PbSe quantum dots. As is known to those of skill in the art, CdSe/ZnS means that a ZnS shell is coated on a CdSe core surface (i.e.: "core-shell" quantum dots). The shell materials of core-shell QDs have a higher band gap and passivate the core QDs surfaces, resulting in higher quantum yield and higher stability and wider applications than core QDs.

As used herein, the term "population" with regard to fluorophores, including QDs, refers to a plurality of fluorophores sharing a common wavelength of maximum emission and intensity.

As used herein, "barcode" refers to a bead or microbead containing one, two, three or more populations of fluorophores. It may be possible to have a single population of fluorophores emitting a single color, if the intensity of the fluorophore is varied to achieve multiple sub-populations. Each bead contains a unique optical signature that identifies a surface conjugated molecule. The suitable fluorophores may include organic fluorophores, QDs, multi-metal rods or any other fluorophore capable of forming an optical signature. Approximately 10,000 to 40,000 different barcodes can be engineered using 5-6 different color quantum dots and six intensity levels (9). This enables significant multiplexing and these barcodes can detect targets in a flow cytometer (10-13) or microfluidic channel (14, 15).

The term "sample" includes both solid and fluid samples. Solid type samples may be solubilized in a suitable fluid. The samples may be biological and/or environmental (i.e. non-biological). Biological samples (fluid or solid) may include samples taken from an organism (unicellular or multicellular) of the animal or plant kingdoms, including prokaryote and eucaryote organisms. Non-fluid samples may be solubilized in a suitable solution. Environmental samples (fluid or solid) may include water samples, soil samples, mineral samples and so forth.

As used herein, "seeding" refers to the addition of metal particles or ions to the bead surface that serve as a nucleating site for the formation of the metal shell around the bead.

In this document, the term "shelf-life" refers to the ability of beads, and barcodes to remain intact in various environmental conditions such as buffer types, solution pH ranges, and temperature ranges and maintain their fluorescence signals in response to these variable environmental cues.

Metal Nanoshell-Coated Barcodes

Described herein is a novel and non-obvious nanoshell-coated barcode with improved stability and improved analytical sensitivity, and methods of preparing the metal nanoshell-coated barcodes.

In one embodiment, the barcode of the present invention includes a metal nanoshell-coated microbead having one or more populations of fluorophores.

The microbead may be a polymeric bead made of a single polymer system or a mixed polymer system. The polymer may be any suitable polymer, including polystyrenes of different molecular weights and other polystyrene (random- or block-) copolymers, including analogues or derivatives. The single polymer bead may be any suitable polymer. In one embodiment, the single polymer bead may be made of poly(styrene-co-maleic anhydride), an analogue or derivative. The mixed polymer system may include a mixture of polymers. In one embodiment, the mixture of polymers may be polystyrene and poly(styrene-co-maleic anhydride) or a mixture of their analogues or derivatives. The ratio between polystyrene and poly(styrene-co-maleic anhydride) (or their analogues or derivatives) may be varied from 4:1 to 1:1 in mass.

The nanoshell may be made of a metal. Metals that may be used include silver and gold. Any other suitable metal capable of forming a shell on the surface of the barcode microbead that provides substantial shelf life and substantial analytical sensitivity may also be used.

The metal nanoshell-coated barcodes of the present invention may be functionalized with target specific capture probes as described herein below.

Method of Preparing Metal Nano-Shell Coated Barcodes

In one embodiment, the present invention provides for a method of preparing a metal nanoshell on barcodes. In one embodiment, the method may include: (a) contacting or seeding one or more populations of barcodes with metal nanoparticles, and (b) mixing the barcodes seeded with the metal nanoparticles with a salt of the metal.

In one embodiment of the method of the present invention, the method may also include conjugating a target-specific capture probe to the metal nanoshell.

In one embodiment of the method, the fluorophores may be polystyrene-coated QDs. In another embodiment, the QDs may be modified with a range of hydrophobic polyaromatic polymers that are similar in structure to the matrix polymer making up the internal regions of the microbead.

Preparation of Barcodes

Figure 1:
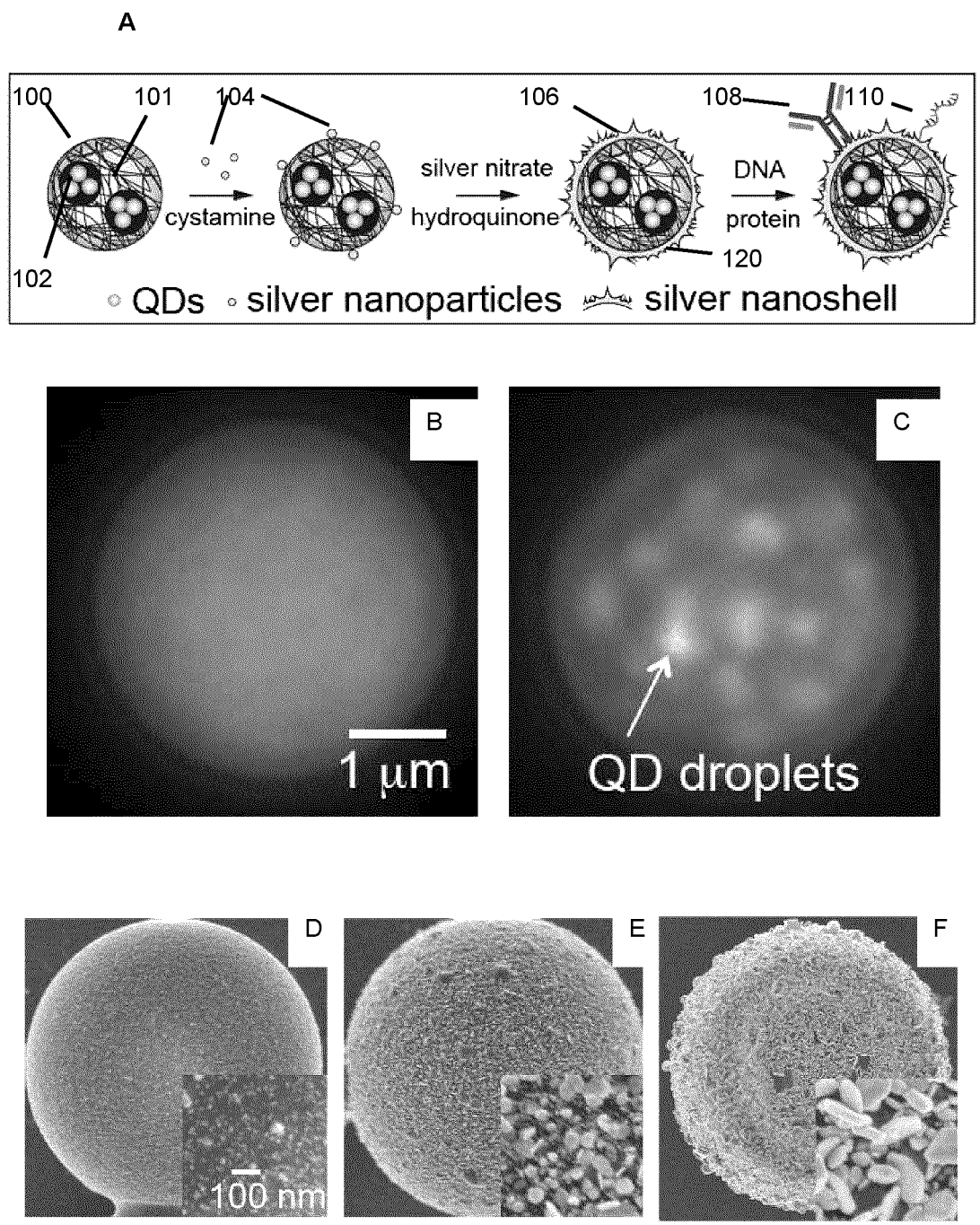
FIG. 1 illustrates the morphology and fluorescence of silver nanoshell-coated quantum dot (QD) microbeads in accordance to one embodiment of the present invention. (A) Scheme that illustrates the process of fabricating and functionalizing silver nanoshell-coated QD microbeads. (B, C) Fluorescence images of uncoated microbeads containing QD555 ($\lambda$em=555 nm) made from (B) poly(styrene-co-maleic anhydride) single polymer or (C) poly(styrene-co-anhydride)-polystyrene mixed polymers. (D-F) Scanning electron microscopy images (obtained at 2 kV) of microbeads with a silver nanoshell growing for different durations. (D) Beads seeded with 10-nm silver nanoparticles grown for 0 minutes. (E) grown for 30 min, average d=70 nm, (F) grown for 120 min, average d=150 nm. (B-F) Scale: single image size is 4×4 μm, and inset image size is 500×500 nm. (G-I) Fluorescence images of silver nanoshell-coated microbeads containing (G) QD510, (H) QD575 and (I) QD665. The thickness of the silver nanoshells was all approximately 50 nm. Single image size is 40×40 μm. All the fluorescence images were acquired through a long-pass (>430 nm) filter with a mercury lamp excitation ($\lambda$ex=350/50) and 100× UPlanApo objective (NA=1.35). (J) Graph showing the correlation of the fluorescence intensity of beads with the thickness of the silver nanoshell. The fluorescence intensity of uncoated beads was converted to 100% and other groups were normalized accordingly.
Figure 1:
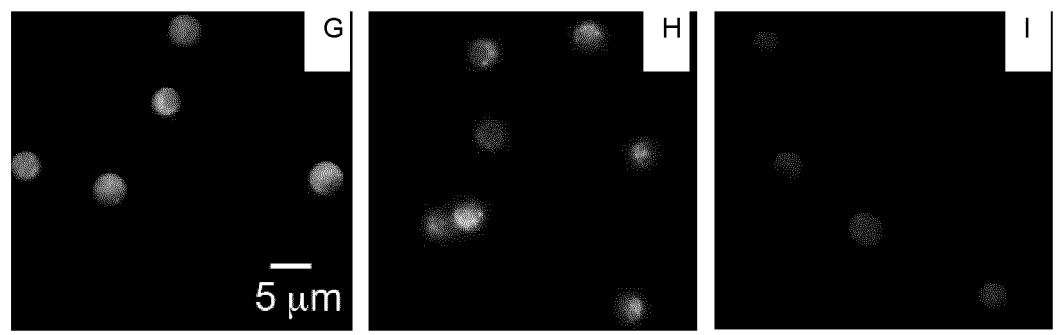
Figure 1:
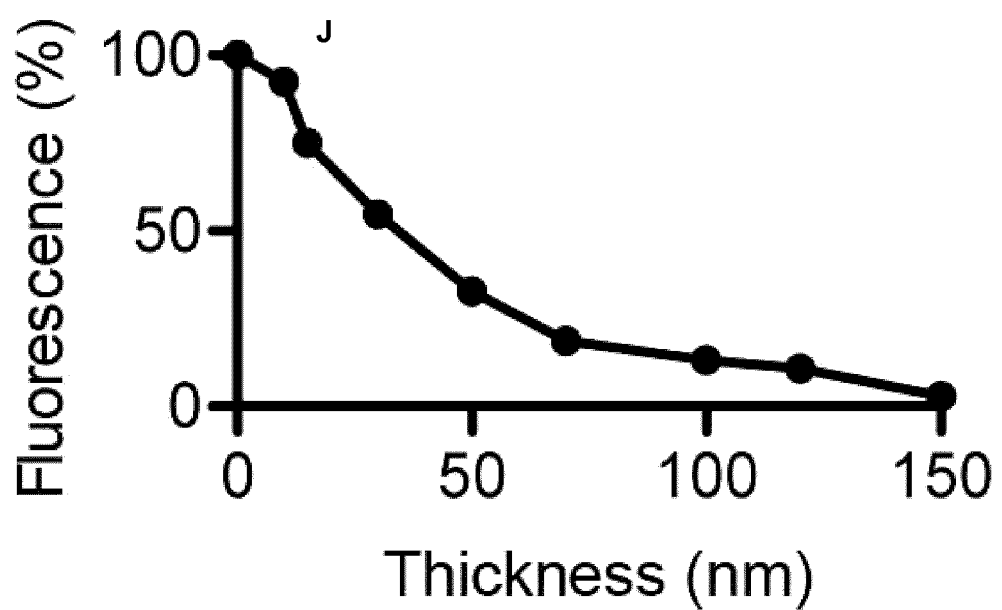

An embodiment for preparing the metal nano-shell coated barcodes of the present invention is illustrated in FIG. 1A.

With reference to FIG. 1A, a barcode may include a microbead 101 having one or more populations of fluorophores 102. The barcodes 100 may be made by any method known in the art, such as by the concentration-controlled flow focusing (CCFF) technique [2]. Fluorophores 102, such as QDs, may be mixed with a single polymer system to form a single polymer barcode, or with a mixed-polymer system, to form a mixed polymer barcode. The single polymer system may be made of any suitable polymer such as poly(styrene-co-maleic anhydride) alone. The mixed polymer system may be made of a mixture of two or more different polymers. In one embodiment, the mixed polymer system may be made of poly(styrene-co-maleic anhydride) and polystyrene. Other polymers that may also be used to make beads, in single or mixed polymer system, include polystyrenes of different molecular weights and other polystyrene (random- or block-) copolymers. The ratio between polystyrene and poly(styrene-co-maleic anhydride) may be varied from 4:1 to 1:1 in mass.

Fluorophores used to prepare the barcodes may be coated with amino terminated polystyrene polymers. Polystyrene-coated QDs may be prepared by any of the known methods in the art [1]. In one embodiment, QDs may be provided as tri-n-octylphosphine oxide (TOPO) QDs. Using TOPO QDs as an example, the TOPO ligands on the QD surface may be replaced with amino-terminated polystyrene polymers, thereby obtaining the polystyrene-coated QDs. A ligand exchange process may be used to replace the TOPO ligands with amino-terminated polystyrene polymers. Other methods for modifying the surface chemistry of quantum dots include ligand exchange with monodentate or multidentate thiol-, phosphine-, or aminated ligands; polymer encapsulation; silanization. Any of these methods could be used to produce surface-modified quantum dots.

FIG. 1B and FIG. 1C are SEM photographs illustrating uncoated microbeads containing QDs made from single polymer (FIG. 1B) and mixed polymers (FIG. 1C) imaged under a wide-field microscope. QDs appear to be evenly distributed in the single-polymer beads (FIG. 1B), while they appear to be sequestered into small droplets when a mixture of polymers is present (FIG. 1C).

Growth of a Metal Nanoshell on the Surface of Microbeads

With reference to FIG. 1A a metal nanoshell 106 may be grown on the surface of the single polymer or mixed polymer barcodes 100. Growth of the metal nanoshell 106 includes seeding polymeric microbeads 101 (single polymer or mixed polymer) of barcodes 100 with metal nanoparticles 104, and growing the metal nanoshell 106 on the surface of the microbeads 101 by the addition of a reducing agent and a salt of the metal to form a metal nanoshell-coated barcode 120. The metal nanoshell-coated barcode may be functionalized with one or more capture probes 108, 110, which may be attached to the metal nanoshell-coated barcode 120 as it will be described herein below.

To grow a metal nanoshell, the microbead surface of the barcodes may be enriched with groups having enhanced affinity to metal nanoparticles used for the seeding process. In one embodiment, this enrichment step may be achieved by enriching the surface of the microbeads with thiol or sulphydryl groups. The microbead surface of the barcode may be provided with carboxylic groups for surface functionalization. For example, carboxylic groups may be formed by the maleic anhydride. In one embodiment, carboxylic acid functional groups of the microbeads' surface may be modified with cystamine for example via a carbodiimide-mediated reaction. The thiolated microbeads may then be incubated with metal nanoparticles as a seeding process (See FIG. 1D). Most commercially available microbeads rely on carboxyl groups for surface functionalization; however, amine functionalized microbeads are also available. To thiolate amine microbeads, thioglycolic acid or amine-reactive esters containing thiol groups may be used instead of cystamine. Microbeads made of pure polystyrene have a hydrophobic surface that may absorb proteins. A protein layer may be formed on the bead surface after incubation with polystyrene beads. This protein layer has high affinity to metal nanoparticles used for seeding purpose in the seeding steps.

The diameter of the metal nanoparticles may range between 6 to 12 nm. In one embodiment, the metal nanoparticles, may have an average diameter of 6 nm, in another embodiment of 7 nm, in another embodiment of 8 nm, in another embodiment of 9 nm, in another embodiment of 10 nm, in another embodiment of 11 nm, in another embodiment of 12 nm. The metal nanoshell may be grown on the surface of the microbeads of the barcodes by the addition of a reducing agent and a salt of the metal being used. In the case of silver, the metal salt may be silver nitrate, in the case of gold, the metal salt may be gold chloride. The metal shell thickness and surface coverage on the microbead surface may be tuned or controlled with prolonged or reduced growth time, and with continuous addition of reducing agent and silver nitrate/gold chloride. The growing time may range from 0 minutes (see FIG. 1D) to up to 2 hours (see FIG. 1F). More than two hours may also be possible. The thickness of the nanoshell may range from 20 to 80 nm. The ratio of reducing agent to metal salt may be 1:1. This process was characterized under a scanning electron microscope (FIG. 1D-F). The shell thickness increased to 150 nm after two hours of growth. Barcodes containing QDs of different emitting colors may be coated with silver nanoshells of around 50 nm in thickness (FIG. 1G-I). Further detailed images of metal nanoshell growing over time are available in FIG. 6. As such, a standard curve may be developed to compare metal nanoshell thickness and growth time. The standard curve may then be used in a method of manufacturing the barcodes of the present invention having a metal nanoshell of a pre-selected thickness by growing the shell for a growth time that corresponds to the pre-selected thickness.

Detection and Multiplex-Detection Systems

The nanoshell-coated barcodes of the present invention may be suitable in systems and methods for detecting organic or inorganic targets in samples. The metal nanoshell-coated barcodes of the present invention may also be used in methods and multiplex detection systems for the simultaneous detection of multiple organic targets including biological targets, such as pathogens, peptides, proteomic and genomic targets, amino acid sequences, nucleic acid sequences, lipids, polysaccharides and so forth, or inorganic targets such as those containing metal atoms, in a single sample.

As such, in one embodiment, the present invention provides for a method of detecting a target of interest in a sample. The method, in one embodiment, may include: contacting the sample with: (a) a plurality of barcodes, each barcode comprising a metal nanoshell-coated microbead having one or more populations of fluorophores, and a capture probe conjugated to the metal nanoshell, the capture probe being capable of interacting with the target of interest, each barcode being capable of emitting a target-specific signal, and (b) a secondary probe, the secondary probe being capable interacting with the target of interest and of emitting a secondary probe signal; wherein the presence of the barcode signal and the secondary probe signal indicates detection of the target in the sample.

In another embodiment, the present invention provides for a detection system for detecting a target in a sample. The detection system, in one embodiment, may include a plurality of barcodes, each barcode comprising a metal nanoshell-coated microbead having one or more populations of fluorophores and a capture probe conjugated to the metal nanoshell, the capture probe being capable of interacting with the target and the system being capable of producing a detectable signal that indicates detection of the target in the sample, the detectable signal being comprised of a first signal from the barcode having the capture probe bound to the target and a second signal from a secondary probe bound to the target.

In another embodiment, the present invention provides for a multiplex detection system for simultaneously detecting multiple targets of interest in a single sample. The multiplex detection system of the present invention, in one embodiment, may include: a plurality of barcodes, each barcode comprising: (i) a metal nanoshell-coated microbead having one or more populations of fluorophores and (ii) one capture probe conjugated to the surface of the barcode capable of interacting with one of the multiple targets of interest such that the plurality of barcodes include at least one barcode for each of the multiple targets of interest, the plurality of metal nanoshell-barcodes being capable of producing different target-specific signals for each of the multiple targets of interest, each target-specific signal being comprised of a first signal from the barcode having the capture probe interacting with a particular target of interest, and a second signal from a secondary probe bound to the particular target of interest.

In one embodiment, the detection system or the multiplex detection system may combine the metal nanoshell-coated barcodes of the present invention with wireless communication devices, such as computers, cellular phones, tablets, and watches to enable the simultaneous detection of multiple organic or inorganic targets in a sample. The wireless, multiplex detection systems of the present invention may allow for the detection and quantitative analysis of multiple targets using a wireless communication device having a camera to image the detectable signal from the multiplex detection system. The wireless capabilities of systems and methods of the present invention may allow them to be used in remote settings, enable wireless transmission of data for interpretation, and may allow the mapping and surveillance of target spread.

The wireless communication device may include means for colleting the signals from the barcodes, means to transmit the collected signals, or both.

Advantages

Nanoshell-coated barcodes of the present invention were also shown, as further exemplified herein bellow, to have: substantial fluorescence stability and consistency in different biological environments (see FIG. 2), enhanced shelf-life (see FIGS. 13 and 14), easily conjugated to capture probes (see FIGS. 3 and Table 2), and application as a multiplex detection system of organic or inorganic targets of interest (see FIG. 4).

Other advantages of the nanoshell-coated barcodes of the present invention include: (a) The diameter of microbeads, the fluorescence of QDs, and the thickness of the metal nanoshell are tunable. (b) The fluorescence of the barcodes of the present invention may have substantially greater consistency in a wide range of pH ranges, buffers and temperature conditions. Control over these parameters may lead to improvements in the barcode signal consistency (c) About a 2-order increase in analytical sensitivity for detecting genetic targets using metal nanoshell-coated microbeads has been observed in comparison to uncoated microbeads. The assay process is simple, reliable and relatively fast, and the detection sensitivity is comparable to other bead-based detection platforms with signal amplification mechanisms [29,30]. (d) Microbeads are capable of multiplexed detection with excellent barcoding performance. The inventors show that the barcodes may be used to differentiate the potentially deadly Plasmodium falciparum malaria pathogen from less deadly malaria species, such as Plasmodium vivax. These advantages make this platform an ideal candidate for ultra-sensitive and high-throughput multiplexed sensing applications in a wide variety of fields.

In order that this invention may be better understood, the following examples are set forth. These examples are for purposes of illustration only and are not to be construed as limiting the scope of the invention in any manner.

EXAMPLES

Experimental Procedures

QD synthesis: tri-n-octylphosphine oxide(TOPO)ZnS-capped CdSe QDs were synthesized and characterized based on published procedures [31] and stored in chloroform. The quantum yields of QDs were between 0.2 to 0.4 depending on the batch.

Ligand exchange on QD surface: the chloroform of TOPO-coated QDs solution was evaporated by a gentle air stream. Amino-terminated polystyrene polymer (Mn=5000, from Polymer Source) and QDs (molar ratio =1000:1) were dissolved in toluene and incubated at 60° C. overnight. Polystyrene-coated QDs were precipitated by adding methanol and re-suspended in chloroform for bead synthesis.

Synthesis of QD barcodes: QD barcodes were synthesized by the concentration-controlled flow focusing (CCFF) technique modified from a pervious report [32]. Polystyrene-coated QDs were mixed with poly(styrene-co-maleic anhydride) polymer alone (4%, w/v) or poly(styrene-co-maleic anhydride)(2%)-polystyrene (2%) mixed polymers in chloroform. The solution was filtered through a 0.2-μm PTFE filter and then injected into a customized nozzle system (Ingeniatrics) at a rate of 1.2 mL/hour by a syringe pump (World Precision Instruments) along with the focusing fluid (water) at a rate of 180 mL/hour by a digital gear pump (Cole Parmer Instruments). The bottom of the nozzle was immersed in water. After synthesis, the QD barcodes were hardened by overnight stirring and collected by centrifugation. The size and concentration of barcodes were determined by a Vi-Cell analyzer (Beckman Coulter).

Growth of a metal nanoshell on barcode surface: 1 million QD barcodes were incubated with 100 μL of EDC (20 mg/mL in MES buffer of pH 6.5, 50 mM) and 30 μL of cystamine (50 mM in MES buffer) at room temperature for 4 hours. Excess cystamine was washed off in water by repeated centrifugation at 5,000 g for 5 minutes. Thiolated beads were incubated with silver or gold nanoparticles (average diameter=10 nm, 100 μL of 100 nM in 1 mM citrate from Nanocomposix) overnight at room temperature. The metal nanoparticles acted as a nucleation site for growth of metal. Barcodes were then washed in water (containing 0.05% TWEEN-20) by repeated centrifugation at 500 g for 5 minutes. Silver or gold-seeded barcodes were re-suspended in 50 μL of silver nitrate or gold chloride (1 mM) respectively, and hydroquinone (1 mM) for up to 2 hours, and washed in water (0.05% TWEEN-20) by repeated centrifugation at 100 g for 5 minutes. Metal nanoshell-coated beads were stored in water at 4° C.

Scanning electron microscopy (SEM) imaging: metal nanoshell-coated barcodes were dropped on a carbon-film coated grid (300 mesh from Ted Pella) and imaged by a Hitachi S-5200 SEM at 2.0 kV.

Functionalization of barcode surface with DNA capture probes: The procedure for functionalization of the barcode surface with DNA probes was modified from a published report [33]. 1 million beads were incubated with 50 μL of thiolated capture probe (30 μM in PBST containing 0.9 M of sodium chloride) at room temperature for 2 hours. Barcodes were washed in water (0.05% TWEEN-20) by repeated centrifugation at 100 g for 5 minutes. For uncoated beads, the conjugation condition was previously optimized [34]. 1 million uncoated beads were incubated with aminated capture probe (same amount as the thiolated capture probe used for silver nanoshell-coated barcodes) and EDC (10 mg in 100 μL of MES buffer pH 5.0, 100 mM) over-night at room temperature. Barcodes were then washed in water by repeated centrifugation at 5000 g for 5 minutes. The amount of capture probe on beads were calculated by measuring the remaining DNA amount in the supernatant after conjugation and centrifugation, and subtracting from the total amount of capture probes. The same amount of capture probes was used for uncoated and silver-nanoshell coated beads during the conjugation process. The amount of capture probe per bead is shown in Table 2.

DNA assay: for each sample, about 5,000 microbeads were incubated with different concentrations of target DNA strand and Alexa647-labeled secondary probe in hybridization buffer (5×SSC buffer from Sigma) with a final volume of 20 μL. The amount of reporter probe was in 100 times molar excess of the highest target amount in the assay. The reaction was carried out at 40° C. for 20 minutes in a HL-2000 HybriLinker hybridization oven (UVP), followed by washing through a 96-well 0.45-μm filter plate (Millipore). Microbeads were then resuspended in PBST and analyzed by a flow cytometer (BD Biosciences).

Sequences of DNA strands: DNA strands were synthesized by IDT or Bio Basic.

TABLE 1

| | Capture probe 5'-end to 3'-end direction | Target 5'-end to 3'-end direction | Secondary probe (5'-AF647) 5'-end to 3'-end direction |
|---|---|---|---|
| Negative control | SEQ ID NO: 1 aaaaaaaaag acaatgctca ctgaggatagt | SEQ ID NO: 2 cggcgatgaatac ctagcacacttac taactatcctcag tgagcattgtc | SEQ ID NO: 9 Taagtgtgctagg tattcatcgccg |
| Positive control | SEQ ID NO: 3 aaaaaaaaac caatatcggc ggcc | SEQ ID NO: 4 cggcgatgaata cctagcacactt actaggccgc cgatattgg | |
| P. falciparum | SEQ ID NO: 5 aaaaaaaaaaa tatatttggtt ttcccaaac cagtttaa | SEQ ID NO: 6 cggcgatgaata cctagcacactt actattaaactg gtttgggaaaac caaatatatt | |

TABLE 1-continued

| | Capture probe 5'-end to 3'-end direction | Target 5'-end to 3'-end direction | Secondary probe (5'-AF647) 5'-end to 3'-end direction |
|---|---|---|---|
| P.vivax | SEQ ID NO: 7 aaaaaaaagt atcagttatg tggattaag ctagaagcg | SEQ ID NO: 8 cggcgatgaatac ctagcacacttac tacgcttctagct taatccacataac tgatac | |

Results

Fluorescence Intensity of the Metal Nanoshell-Coated Barcodes

The fluorescence intensity of metal-coated QD barcodes of the present invention was shown to remain distinct under a wide field microscope. It has also been shown that a metal nanoshell with controlled thickness may not substantially affect the barcoding capacity of QDs. The fluorescence intensities of QD microbeads of the present invention decreased with increased shell thickness (see FIG. 1J) since fewer photons may be able to penetrate into and through the microbeads with a thicker shell.

As shown in FIGS. 7, 8 and 9 the decreasing fluorescence with respect to an increase in metal nanoshell thickness was similar for single and mixed polymer barcodes, and also for barcodes containing different emitting QDs. FIG. 7 is a graph illustrating the effect of silver nanoshell thickness on the fluorescence intensity of mixed-polymer QD barcodes. Similar to FIG. 1J, a silver nanoshell was grown on barcodes made of mixed polymers for different periods of time and measured by flow cytometry. The median fluorescence intensity of uncoated beads were normalized to 100%.

FIG. 8 includes graphs that illustrate the effect of silver nanoshell growing time on (A) the fluorescence intensity of QD600 barcodes, and (B) forward scattering. A silver nanoshell was grown on microbeads containing QD600 for different periods of time and measured by flow cytometry. The median fluorescence intensity and the forward scattering (FSC) values of uncoated beads were normalized to 100%, respectively. The silver nanoshell reduced the fluorescence intensity of QD600 barcodes in a similar manner to QD555 barcode in FIG. 1i (panel A). The FSC value increased over growing time, reflecting bigger diameters of microbeads added by silver nanoshells (FIG. 8B).

Figure 9B:
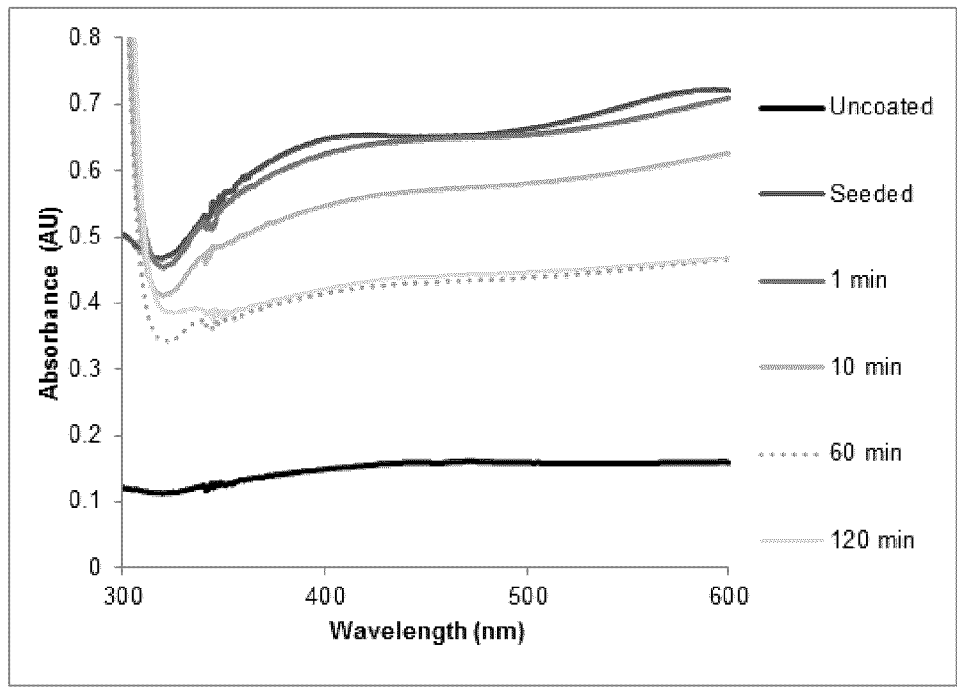

FIG. 9 illustrates (A) fluorescence and (B) absorbance spectra of QD barcodes during silver nanoshell growing. The fluorescence spectrum of the same sample was recorded by a fluorometer during silver nanoshell growing. The excitation wavelength was set at 450 nm. The emission peak of QD barcodes was constant at 555 nm throughout the growing time of silver nanoshells (FIG. 9A). The absorbance of the same sample was also recorded by a spectrometer (FIG. 9B).

As shown in FIG. 9, the metal nanoshells only decreased the fluorescence intensity of QD barcodes, but did not shift their emitting wavelength. Therefore, in practical applications the thickness of the nanoshells may be controlled to allow the fluorescence to be excited and captured by a camera or photodetectors. This would allow for proper identification of the barcodes.

Different shell thicknesses may also be used to increase the number of QD barcodes since the thickness would influence the fluorescence intensities.

FIG. 11 includes graphs illustrating the effect of gold nanoshell growing time on (A) fluorescence intensity of QD barcodes and (B) forward scattering of QD barcodes. In the case of FIG. 11, QD barcodes were coated with a gold (Au) nanoshell for different periods of time and measured by flow cytometry. The median fluorescence intensity and the FSC values of uncoated beads were normalized to 100%, respectively. The results were similar to those obtained with the silver nanoshell. The fact that silver nanoparticles absorb around 420 nm may provide for a relatively greater selection of secondary fluorophores.

Fluorescence Stability of the Metal Nanoshell-Coated Barcodes

FIG. 12 shows graphs illustrating fluorescence stabilities of uncoated QD barcodes made of single polymer and mixed polymers under different conditions: pH (FIG. 12A), buffer (FIG. 12B), and temperature (FIG. 12C). The median fluorescence intensity of microbeads at pH 7, water and 25° C. were normalized to 100% separately for each condition. As illustrated in FIG. 12, the barcode fluorescence of the two compositions showed similar trends in these conditions.

Figure 2:
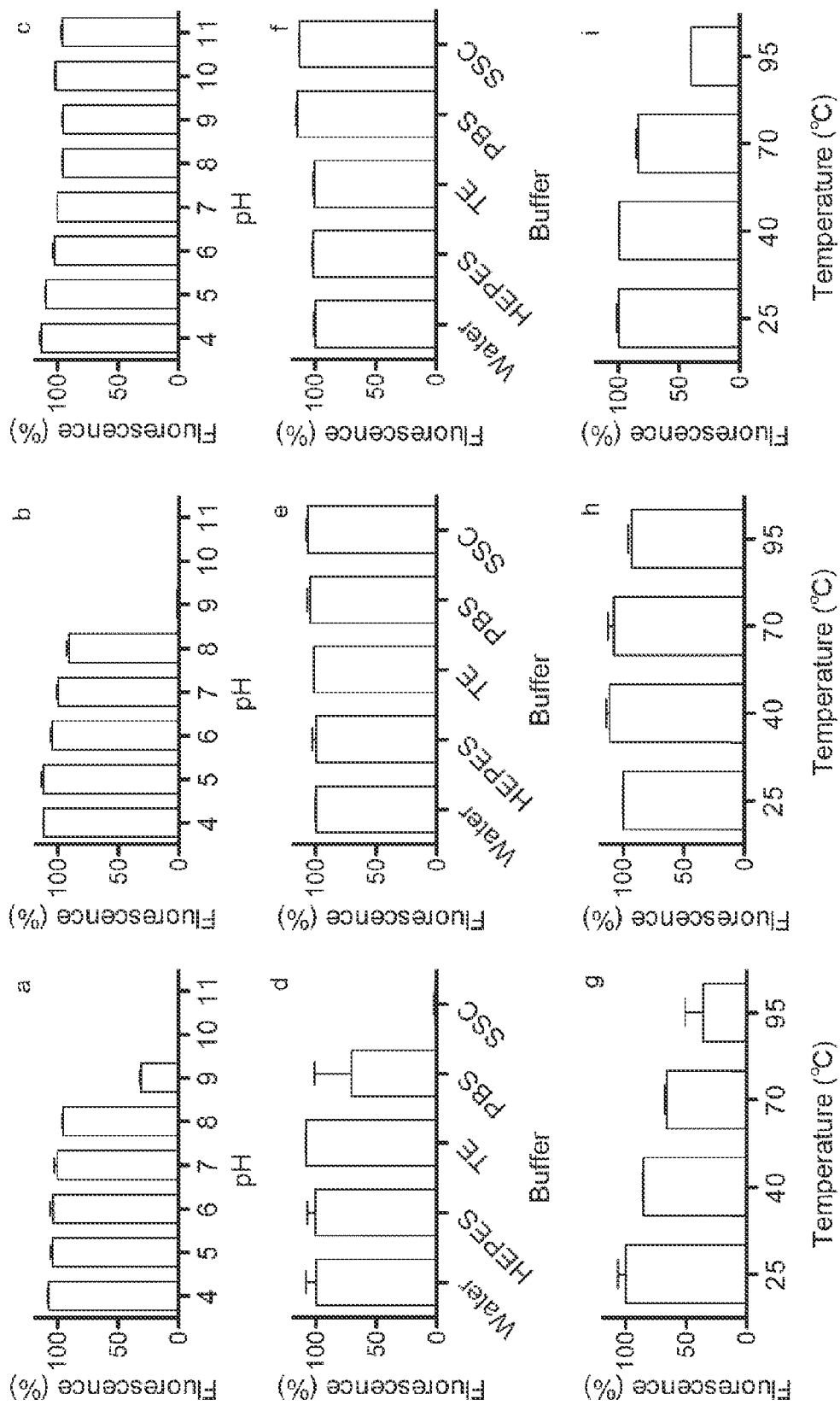
FIG. 2 are graphs illustrating the fluorescence stabilities of QD microbeads made from different compositions under environmental conditions. Left column (graphs a, d, g): uncoated poly(styrene-co-maleic anhydride) single polymer; middle column (graphs b, e, h): silver nanoshell-coated single polymer.

Uncoated single polymer QD barcodes were compared with silver nanoshell-coated single and mixed polymer barcodes. Uncoated mixed polymer barcodes were not compared because, as previously shown, the polymer composition did not significantly affect their shelf-life (see FIG. 12). FIG. 2 illustrates the fluorescence stability of the QD microbeads made from the different compositions. The silver nanoshells were 20-30 nm in thickness. Microbeads were incubated in pH 4 to 11 for 24 hours (a-c), or in water, HEPES (pH 7), TE (pH 8), PBS (pH 7) and SSC (pH 7) buffer for 24 hours (d-f), or in 25° C. to 95° C. for 20 minutes (g-i). The median fluorescence intensities of microbeads were determined by flow cytometry after treatment. In each condition, the intensity values of microbeads at pH 7, water and 25° C. were converted to 100% and other groups were normalized accordingly. As illustrated in FIG. 2, the fluorescence of uncoated single-polymer beads dropped dramatically at pHs above 8, buffers with a salt concentration of over 100 mM, and temperatures over 40° C. (FIG. 2a, d, g). Compared to uncoated beads, a silver nanoshell significantly improved the fluorescence stability of both the single and mixed polymer microbeads under tested buffer and temperature conditions.

Shelf-Life of Metal Nanoshell-coated Barcodes

Microbeads were incubated in pH 4 to 11 for 24 hours (FIG. 13, a-c), or in water, HEPES (pH 7), TE (pH 8), PBS (pH 7) and SSC (pH 7) buffer for 24 hours (FIG. 13, d-f), or in 25° C. to 95° C. for 20 minutes (FIG. 13, g-i). These samples were the same samples as in FIG. 2. The numbers of intact beads under different conditions were determined by the forwarding scattering (FSC)-side scattering (SSC) plots in flow cytometry and summarized as above (FIG. 14). In each condition, the numbers of intact microbeads at pH 7, water and 25° C. were converted to 100% and other groups were normalized accordingly. Results are illustrated in FIGS. 13 and 14.

The forward scattering and side scattering plots suggest that uncoated beads degraded easily under alkaline, high ionic strength, and high heat conditions (see FIG. 14). With a silver nanoshell, microbeads remained intact under these conditions. FIG. 14 illustrates that uncoated single-polymer beads degraded dramatically at pH 11. There was no obvious shift in the silver-nanoshell coated mixed-polymer bar-codes in all pHs. The plots of microbeads in buffers and temperatures showed similar results as above. Silver nanoshell-coated single-polymer beads were intact but their fluorescence was changed by high pHs (FIG. 2b). Beads made of mixed polymers with silver nanoshells appear to demonstrate optimal compatibility with pH from 4 to 11, all buffers, and temperatures up to 70° C. (FIG. 2c, f, i). The unique phase-segregated domains within the microbeads prevented aqueous ions from contacting and interacting with the QDs. Therefore, both the silver nanoshells and mixed polymers appear to be important in achieving the better fluorescence stability and bead structure of the QD barcodes.

As shown in FIG. 15, gold nanoshell (about 50 nm in thickness) demonstrated a similar protective effect on the barcodes as did the silver nanoshell. Both beads were made from single polymer.

Applications of the Metal Nanoshell-Coated Barcodes

The metal nanoshell-coated barcodes of the present invention may be functionalized by conjugating a capture probe to the surface of the metal nanoshell.

The inventors compared the analytical performance of uncoated and silver nanoshell-coated microbeads in detection assays. The positive control DNA strand (cggcgatgaatacctagcacacttactaggccgccgatattgg) (SEQ ID NO: 4) used in the multiplexed experiments was chosen as the model target. Uncoated QD555 beads were conjugated with an aminated capture probe of the target strand (aaaaaaaaaccaatatcggcggcc) (SEQ ID NO: 3) by a carbodiimide coupling agent. The conjugation conditions were optimized in previous studies [16,17] Briefly, 1 million of uncoated beads were incubated in 100 pL of MES buffer (pH 6.5, 50 mM) containing 10 mg of EDC and 28 picomole of capture probe over night. Silver nanoshell-coated beads were functionalized with thiolated capture probe. The amount of capture probes for conjugation was kept constant between the uncoated and silver nanoshell-coated QD barcodes. The target strand was then measured by a sandwich assay using both types of beads performed in parallel (FIG. 3A). The sandwich assay refers to the binding of the target to both the capture probe on the barcode and the secondary probe. After washing steps during the assay to remove unbound material (barcodes may be washed after capture probe conjugation to the surface of the barcode, after the barcode with capture probe is incubated with the target, and after the barcode and target complex is incubated with the secondary probe), the presence of signals from both the barcode and the secondary probe indicate successful capture of the target.

Silver nanoshell-coated beads exhibited a detection limit of 3 attomoles, which was a 2-order improvement over uncoated beads (see FIG. 3B). This detection sensitivity was achieved by a 1-step 20-minute sandwich assay without any signal amplification. These findings are the first results demonstrating that a metal nanoshell on microbead surface significantly improves the detection sensitivity of biosensing. There were several potential mechanisms contributing to the signal enhancement. First, there were about 3 times more capture probes on each silver-nanoshell coated bead than the un-coated bead (see Table 2). As a result, the target strands would have a higher chance to be captured by the silver nanoshell-coated barcodes. But the increase amount of capture probes on the bead surface is obviously not sufficient to account for the whole increase in detection sensitivity. One mechanism may be that the surface of silver nanoshells is slightly roughened. For uncoated beads, the inventors found steric effects of the capture probe influenced the analytical sensitivity [16]. Therefore, the capture probe on a roughened surface tends to be slightly disordered, which minimizes the steric interactions between the target molecules with the capture probes. The inventors also found uncoated beads significantly disintegrated under various conditions, leading to reduced assay signals. Consistent with the results shown in FIG. 2, silver nanoshells increased the barcode stability under the assay conditions. This may contribute to the improved assay performance. The uncoated beads also showed a higher level of non-specific binding of secondary probes compared to the silver nanoshell-coated beads, leading to a higher background signal and reduced detection sensitivity (FIG. 3). Another possible factor may be the metal enhanced fluorescence effect of reporter fluorophores by the silver nanoshell. Silver nanoparticles can enhance the fluorescence intensity of fluorophores in a distance- and thickness-dependent manner [18,19]. For Alexa647, the secondary fluorescent probe used in the assays of the Examples, strong metal enhanced fluorescence can occur at a distance of 15 to 50 nm away from the silver nanoparticles of a thickness/diameter of 10 to 150 nm [20,21]. In the present design, the distance between Alexa647 and the silver nanoshell was about 25 nm based on the lengths of the capture probe and reporter probe (sequences available in Table 1), which is within the range of metal enhanced fluorescence. It is likely the combination of the above and other unknown factors that lead to the final enhancement of detection sensitivity.

Multiplex Detection System

The inventors further demonstrated the practical application of the metal nanoshell-coated QD barcodes of the present invention in multiplexed detection by conducting a 4-plex DNA assay for differentiation of *Plasmodium falciparum*, a potentially deadly species of malaria, from other nonlethal malaria species.

Over 1 million people die from malaria infections annually [22,23]. There are four different parasites that cause malaria in humans: *P. falciparum, P. vivax, P. ovale*, and *P. malariae*. The ability to differentially identify the potentially deadly *P. falciparum* from the other species is important for proper clinical treatment of patients and to reduce drug resistance.

In order to detect *P. falciparum* from other malarial species, capture probes were designed based on genetically conserved regions of the 18S rRNA gene of *P. falciparum* and *P. vivax* [24,25], and an Alexa647-labeled sequence was used as a secondary probe. Negative and positive control strands were also designed (the DNA sequences are available in Table 1). Silver nanoshell-coated QD barcodes of four different fluorescent signatures were functionalized with thiolated capture probes for each target [26].

The dose-response curves of *P. falciparum* and *P. vivax* are shown in FIGS. 4a and 4b. Both target strands showed excellent linearity between their concentration and the assay signal. The signal intensity of *P. vivax* is about ten times higher than that of P. falciparum. Similar differences were observed by the inventors in other studies as well [16]. The difference in assay signals among strands is related to the sequences of DNA, because the composition of nucleotides affects the melting temperature and binding affinity leading to variance in assay efficiencies. Different DNA targets exhibit different assay signal intensities, caused by the differences in secondary structures of capture probes and target strands, and conjugation efficiencies. To investigate the cross-reactivity among target strands, five different mock genetic samples were prepared by mixing different combinations of the target strands plus a positive control strand (10 femtomoles). There was negligible nonspecific binding of the reporter probe to silver nanoshell-coated beads as shown in the all-negative group. The target strands did not affect each other's signal, suggesting no cross-reactivity between the strands (FIG. 4c). The present results clearly demonstrate the ability of these barcodes to differentiate different strains of malaria parasites in a single reaction vial. The current gold standard method for differentiating malaria species is lateral flow assays using protein biomarkers [27]. This clinically approved technique can only detect *P. falciparum* and the other malarial species at high parasitemia (i.e. parasite burden in the blood) but are much less reliable in infections with low parasitemia [28]. PCR diagnostic techniques have much better analytical sensitivity than later flow assays and can differentiate malarial species but PCR will be difficult for use in the field or remote settings. The analytical sensitivity of the metal nanoshell-coated barcodes of the present invention is close to that of PCR but bead assays may be easily automated and detected using microscopy, fluorometer, and flow cytometry. Hence, the bead assays have much greater probability of being used in the field in comparison to PCR.

The inventors also studied if metal nanoshells in general can enhance the assay performance. As shown in FIG. 16, gold and silver nanoshells (~50 nm in thickness on ~3 micron beads) were formed on the barcodes. Both nanoshells enhanced the assay performance compared to the uncoated barcode, and silver nanoshells exhibited better signal than the gold nanoshells. FIG. 17A shows the fluorescence spectra of the 4-plex barcodes used in the multiplex assays.

QD540 and QD580 were used to make the 4-plex barcodes and their emission spectra were shown in FIG. 17B. These barcodes showed distinct fluorescence intensity distributions in flow cytometer plots (FIG. 17C). The horizontal scale is the FITC channel (525 nm) intensity. The vertical scale is the PE channel (575 nm) intensity. Barcode 1 (B1) and 4 (B4) were the negative and positive control, respectively. B2 and B3 represent *P. vivax* and *P. falciparum*, respectively. We measured the densities of DNA capture probes on bead surface. As shown in Table 2, the silver nanoshell-coated barcodes had a significantly higher DNA density than the uncoated barcode. FIG. 18 is a table illustrating the amounts of capture probes on uncoated beads and silver nanoshell-coated beads.

TABLE 2

Amount of Capture Probe on Beads

|  | Uncoated beads | Silver nanoshell-coated beads |
|---|---|---|
| Amount of capture probe per bead (attomole) | 54 | 181 |

Presented herein are nanoshell-coated QD barcodes and methods to synthesize metal nanoshell-coated QD barcodes. The diameter of microbeads, the fluorescence of QDs, and the thickness of metal nanoshell may be highly tunable. The fluorescence of the QD barcodes of the present invention has greater consistency in a wide range of pH, buffer and temperature conditions compared with uncoated beads. This should lead to improvements in the barcode signal consistency. The inventors demonstrate at least a 2-order increase in analytical sensitivity for detecting genetic targets using metal nanoshell-coated microbeads in comparison to uncoated microbeads. The assay process is very simple, reliable and fast, and the detection sensitivity is comparable to other bead-based detection platforms with signal amplification mechanisms [29,30]. Finally, it has been shown herein that such composite microbeads are capable of multiplexed detection with excellent barcoding performance.

The barcodes of the present invention were capable of differentiating the potentially deadly *P. falciparum* malaria pathogen from other malaria species. These advantages make this platform an ideal candidate for ultrasensitive and high-throughput multiplexed sensing applications in a wide variety of fields.

REFERENCES

[1] R. Wilson, A. R. Cossins, D. G. Spiller, Encoded microcarriers for high-throughput multiplexed detection, Angew Chem Int Ed Engl 45 (2006) 6104-6117.

[2] M. Han, X. Gao, J. Z. Su, S. Nie, Quantum-dot-tagged microbeads for multiplexed optical coding of biomolecules, Nat Biotechnol 19 (2001) 631-635.

[3] S. Fournier-Bidoz, T. L. Jennings, J. M. Klostranec, W. Fung, A. Rhee, D. Li, W.C. Chan, Facile and rapid one-step mass preparation of quantum-dot barcodes, Angew Chem Int Ed Engl 47 (2008) 5577-5581.

[4] X. Gao, S. Nie, Doping Mesoporous Materials with Multicolor Quantum Dots, J. Phys. Chem. B 107 (2003) 11575-11578.

[5] D. Wang, A. L. Rogach, F. Caruso, Semiconductor Quantum Dot-Labeled Microsphere Bioconjugates Prepared by Stepwise Self-Assembly, Nano Lett. 2 (2002) 857-861.

[6] X. Gao, W. C. Chan, S. Nie, Quantum-dot nanocrystals for ultrasensitive biological labeling and multicolor optical encoding, J Biomed Opt 7 (2002) 532-537.

[7] J. A. Lee, A. Hung, S. Mardyani, A. Rhee, J. Klostranec, Y. Mu, D. Li, W. C. W. Chan, Toward the Accurate Read-out of Quantum Dot Barcodes: Design of Deconvolution Algorithms and Assessment of Fluorescence Signals in Buffer, Adv. Mater. 19 (2007) 3113-3118.

[8] L. Y. Chou, W. C. Chan, A strategy to assemble nanoparticles with polymers for mitigating cytotoxicity and enabling size tuning, Nanomedicine (Lond) 6 (2011) 767-775.

[9] M. Brust, D. J. Schiffrin, D. Bethell, C. J. Kiely, Novel gold-dithiol nano-networks with non-metallic electronic properties, Advanced Materials 7 (1995) 795-797.

[10] Y. C. Cao, X. F. Hua, X. X. Zhu, Z. Wang, Z. L. Huang, Y. D. Zhao, H. Chen, M. X. Liu, Preparation of Au coated polystyrene beads and their application in an immunoassay, Journal of immunological methods 317 (2006) 163-170.

[11] T. Ji, V. G. Lirtsman, Y. Avny, D. Davidov, Preparation, Characterization, and Application of Au-Shell/Polystyrene Beads and Au-Shell/Magnetic Beads, Advanced Materials 13 (2001) 1253-1256.

[12] J. H. Lee, M. A. Mahmoud, V. Sitterle, J. Sitterle, J. C. Meredith, Facile preparation of highly-scattering metal nanoparticle-coated polymer microbeads and their surface plasmon resonance, J Am Chem Soc 131 (2009) 5048-5049.

[13] K. E. Peceros, X. Xu, S. R. Bulcock, M. B. Cortie, Dipole-dipole plasmon interactions in gold-on-polystyrene composites, J Phys Chem B 109 (2005) 21516-21520.

[14] A. D. Quach, G. Crivat, M. A. Tarr, Z. Rosenzweig, Gold nanoparticle-quantum dot-polystyrene microspheres as fluorescence resonance energy transfer probes for bioassays, J Am Chem Soc 133 (2011) 2028-2030.

[15] W. Shi, Y. Sahoo, M. T. Swihart, P. N. Prasad, Gold nanoshells on polystyrene cores for control of surface plasmon resonance, Langmuir 21 (2005) 1610-1617.

[16] Y. Gao, W. L. Stanford, W. C. Chan, Quantum-dot-encoded microbeads for multiplexed genetic detection of non-amplified DNA samples, Small 7 (2011) 137-146.

[17] S. Giri, E. A. Sykes, T. L. Jennings, W. C. Chan, Rapid screening of genetic biomarkers of infectious agents using quantum dot barcodes, ACS Nano 5 (2011) 1580-1587.

[18] A. I. Dragan, E. S. Bishop, J. R. Casas-Finet, R. J. Strouse, M. A. Schenerman, C. D. Geddes, Metal-enhanced PicoGreen fluorescence: application for double-stranded DNA quantification, Anal Biochem 396 (2010) 8-12.

[19] C. R. Sabanayagam, J. R. Lakowicz, Increasing the sensitivity of DNA microarrays by metal-enhanced fluorescence using surface-bound silver nanoparticles, Nucleic Acids Res 35 (2007) e13.

[20] E. G. Matveeva, I. Gryczynski, A. Barnett, Z. Leonenko, J. R. Lakowicz, Z. Gryczynski, Metal particle-enhanced fluorescent immunoassays on metal mirrors, Anal Biochem 363 (2007) 239-245.

[21] J. Zhang, E. Matveeva, I. Gryczynski, Z. Leonenko, J. R. Lakowicz, Metal-enhanced fluoroimmunoassay on a silver film by vapor deposition, J Phys Chem B 109 (2005) 7969-7975.

[22] Y. Kockaerts, S. Vanhees, D. C. Knockaert, J. Verhaegen, M. Lontie, W.E. Peetermans, Imported malaria in the 1990s: a review of 101 patients, European Journal of Emergency Medicine 8 (2001) 287.

[23] P. Martens, L. Hall, Malaria on the move: human population movement and malaria transmission, Emerging Infectious Diseases 6 (2000) 103.

[24] M. Ndao, E. Bandyayera, E. Kokoskin, T. W. Gyorkos, J. D. MacLean, B. J. Ward, Comparison of blood smear, antigen detection, and nested-PCR methods for screening refugees from regions where malaria is endemic after a malaria outbreak in Quebec, Canada, Journal of clinical microbiology 42 (2004) 2694-2700.

[25] G. Snounou, S. Viriyakosol, X. P. Zhu, W. Jarra, L. Pinheiro, V. E. do Rosario, S. Thaithong, K. N. Brown, High sensitivity of detection of human malaria parasites by the use of nested polymerase chain reaction, Molecular and biochemical parasitology 61 (1993) 315.

[26] H. D. Hill, J. E. Millstone, M. J. Banholzer, C. A. Mirkin, The role radius of curvature plays in thiolated oligonucleotide loading on gold nanoparticles, ACS Nano 3 (2009) 418-424.

[27] M. L. Wilson, Malaria rapid diagnostic tests, Clin Infect Dis 54 (2012) 1637-1641.

[28] M. L. McMorrow, M. Aidoo, S. P. Kachur, Malaria rapid diagnostic tests in elimination settings—can they find the last parasite?, Clin Microbiol Infect 17 (2011) 1624-1631.

[29] S. C. Chapin, P. S. Doyle, Ultrasensitive multiplexed microRNA quantification on encoded gel microparticles using rolling circle amplification, Anal Chem 83 (2011) 7179-7185.

[30] E. Schopf, Y. Chen, Attomole DNA detection assay via rolling circle amplification and single molecule detection, Anal Biochem 397 (2010) 115-117.

[31] Peng, X.; Schlamp, M. C.; Kadavanich, A. V.; Alivisatos, A. P. Journal of the American Chemical Society1997, 119, 7019-7029.

[32] Lee, J. H.; Mahmoud, M. A.; Sitterle, V.; Sitterle, J.; Meredith, J. C. J Am Chem Soc2009, 131, 5048-5049.

[33] Hill, H. D.; Millstone, J. E.; Banholzer, M. J.; Mirkin, C. A. ACS Nano2009, 3, 418-424.

[34] Gao, Y.; Stanford, W. L.; Chan, W. C. Small2011, 7, 137-146.

The priority document and all publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Therefore what is claimed is:

1. A barcode, the barcode comprising a metal nanoshell-coated microbead containing multiple populations of fluorophores and a target-specific capture probe conjugated directly to an external surface of the metal nanoshell, each population of fluorophores in the microbead sharing a common wavelength such that the microbead has a unique optical signature that identifies the target-specific probe conjugated to the metal nanoshell, the metal nanoshell-coated microbead comprising:

a) a mixed polymer having one or more carboxylic acid functional groups for seeding metal nanoparticles and growing the metal nanoshell on the surface of the microbead in a porous distribution to permit fluorescence emission; and b) wherein the metal nanoshell comprises a porous roughened external surface, wherein the mixed polymer comprises polystyrene and poly(styrene-co-maleic anhydride), or analogues or derivatives thereof, in a ratio of 2:1 to 1:1 in mass.

2. The barcode of claim 1, wherein the fluorophores include organic fluorophores, inorganic fluorophores, or a mixture of organic and inorganic fluorophores.

3. The barcode of claim 1, wherein the mixed polymer comprises polystyrene and poly(styrene-co-maleic anhydride), or analogues or derivatives thereof, in a ratio of 1:1 in mass.

4. The barcode of claim 1, wherein the fluorophores are quantum dots (QDs).

5. The barcode of claim 1, wherein the metal is selected from silver or gold.

6. The barcode of claim 1, wherein the target includes inorganic and organic materials.

7. The barcode of claim 6, wherein the organic materials include unicellular and multicellular organisms and any components thereof, peptides, proteins, oligosaccharides, lipids, genes, nucleic acids, amino acids, and wherein the inorganic materials include inorganic molecules having metal atoms.

8. The barcode of claim 1, wherein the metal nanoshell operates to enhance shelf-life of the barcode relative to the barcode without the metal nanoshell.

9. The barcode of claim 1, wherein the metal nanoshell operates to enhance fluorescence stability of the barcode relative to the barcode without the metal nanoshell.

10. The barcode of claim 1, wherein the nanoshell is selected from a silver nanoshell having a thickness of 20-30 nm and a gold nanoshell having a thickness of about 50 nm.

* * * * *

SEQUENCE LISTING

```
<160> NUMBER OF SEQ ID NOS: 13

<210> SEQ ID NO 1
<211> LENGTH: 31
<212> TYPE: DNA
<213> ORGANISM: Artificial sequence
<220> FEATURE:
<223> OTHER INFORMATION: Oligonucleotide sequence modified with a poly A
      repeat unit spacer (9 units) at the5' end
<300> PUBLICATION INFORMATION:
<301> AUTHORS: Kun, Chen; Chou, Leo Y.T.; Song,  Fayi ; Chan,   Warren
      C.W.
<302> TITLE: Fabrication of metal nanoshell quantum-dot barcodes for
      biomolecular detection
<303> JOURNAL: Nano Today
<304> VOLUME: 8
<305> ISSUE: 3
<306> PAGES: 228-234
<307> DATE: 2013-06-01

<400> SEQUENCE: 1
aaaaaaaaag acaatgctca ctgaggatag t                                        31

<210> SEQ ID NO 2
<211> LENGTH: 50
<212> TYPE: DNA
<213> ORGANISM: Artificial sequence
<220> FEATURE:
```

<223> OTHER INFORMATION: Complementary sequence to unmodified hybrid of
      SEQ ID NO 1 and SEQ ID NO 9

<400> SEQUENCE: 2
ctgttacgag tgactcctat caatcattca cacgatccat aagtagcggc         50

<210> SEQ ID NO 3
<211> LENGTH: 24
<212> TYPE: DNA
<213> ORGANISM: Artificial sequence
<220> FEATURE:
<223> OTHER INFORMATION: Oligonucleotide sequence modified with a poly A
      repeat unit spacer (9 units) at the 5' end

<400> SEQUENCE: 3
aaaaaaaaac caatatcggc ggcc                                    24

<210> SEQ ID NO 4
<211> LENGTH: 43
<212> TYPE: DNA
<213> ORGANISM: Artificial sequence
<220> FEATURE:
<223> OTHER INFORMATION: Complementary sequence to unmodified hybrid of
      SEQ ID NO 3 and SEQ ID NO 9

<400> SEQUENCE: 4
ggttatagcc gccggatcat tcacacgatc cataagtagc ggc               43

<210> SEQ ID NO 5
<211> LENGTH: 39
<212> TYPE: DNA
<213> ORGANISM: Artificial sequence
<220> FEATURE:
<223> OTHER INFORMATION: Oligonucleotide sequence modified with a poly A
      repeat unit spacer (9 units) at the 5' end

<400> SEQUENCE: 5
aaaaaaaaaa atatatttgg ttttcccaaa ccagtttaa                    39

<210> SEQ ID NO 6
<211> LENGTH: 58
<212> TYPE: DNA
<213> ORGANISM: Artificial sequence
<220> FEATURE:
<223> OTHER INFORMATION: Complementary sequence to unmodified hybrid of
      SEQ ID NO 5 and SEQ ID NO 9

<400> SEQUENCE: 6
ttatataaac caaagggtt tggtcaaatt atcattcaca cgatccataa gtagcggc   58

<210> SEQ ID NO 7
<211> LENGTH: 39
<212> TYPE: DNA
<213> ORGANISM: Artificial sequence
<220> FEATURE:
<223> OTHER INFORMATION: Oligonucleotide sequence modified with a poly A
      repeat unit spacer (9 units) at the 5' end

<400> SEQUENCE: 7
aaaaaaaaag tatcagttat gtggattaag ctagaagcg                    39

<210> SEQ ID NO 8
<211> LENGTH: 58
<212> TYPE: DNA
<213> ORGANISM: Artificial sequence
<220> FEATURE:
<223> OTHER INFORMATION: Complementary sequence to unmodified hybrid of SEQ ID NO 7 and SEQ ID NO 9

<400> SEQUENCE: 8
catagtcaat acacctaatt cgatcttcgc atcattcaca cgatccataa gtagcggc    58

<210> SEQ ID NO 9
<211> LENGTH: 25
<212> TYPE: DNA
<213> ORGANISM: Artificial sequence
<220> FEATURE:
<223> OTHER INFORMATION: Synthetic
<220> FEATURE:
<221> NAME/KEY: misc_binding
<222> LOCATION: (1)..(1)
<223> OTHER INFORMATION: Oligonucleotide sequence modified with
      fluorophore (AF647) at 5' end

<400> SEQUENCE: 9
taagtgtgct aggtattcat cgccg    25

<210> SEQ ID NO 10
<211> LENGTH: 31
<212> TYPE: DNA
<213> ORGANISM: Artificial sequence
<220> FEATURE:
<223> OTHER INFORMATION: Synthetic
<220> FEATURE:
<221> NAME/KEY: misc_binding
<222> LOCATION: (1)..(1)
<223> OTHER INFORMATION: Oligonucleotide sequence with a dithiol
      modification at the first base of the 5' end

<400> SEQUENCE: 10
aaaaaaaaag acaatgctca ctgaggatag t    31

<210> SEQ ID NO 11
<211> LENGTH: 24
<212> TYPE: DNA
<213> ORGANISM: Artificial sequence
<220> FEATURE:
<223> OTHER INFORMATION: Synthetic
<220> FEATURE:
<221> NAME/KEY: misc_binding
<222> LOCATION: (1)..(1)
<223> OTHER INFORMATION: Oligonucleotide sequence with a dithiol
      modification at the first base of the 5' end

<400> SEQUENCE: 11
aaaaaaaaac caatatcggc ggcc    24

<210> SEQ ID NO 12
<211> LENGTH: 39
<212> TYPE: DNA
<213> ORGANISM: Artificial sequence
<220> FEATURE:
<223> OTHER INFORMATION: Synthetic
<220> FEATURE:
<221> NAME/KEY: misc_binding
<222> LOCATION: (1)..(1)
<223> OTHER INFORMATION: Oligonucleotide sequence with a dithiol
      modification at the first base of the 5' end

<400> SEQUENCE: 12
aaaaaaaaaa atatatttgg ttttcccaaa ccagtttaa    39

<210> SEQ ID NO 13
<211> LENGTH: 39
<212> TYPE: DNA
<213> ORGANISM: Artificial sequence

```
<220> FEATURE:
<223> OTHER INFORMATION: Synthetic
<220> FEATURE:
<221> NAME/KEY: misc_binding
<222> LOCATION: (1)..(1)
<223> OTHER INFORMATION: Oligonucleotide sequence with a dithiol
      modification at the first base of the 5' end

<400> SEQUENCE: 13
aaaaaaaaag tatcagttat gtggattaag ctagaagcg                              39
```